US012638453B2

(12) United States Patent
Allue Blasco et al.

(10) Patent No.: US 12,638,453 B2
(45) Date of Patent: May 26, 2026

(54) METHODS FOR QUANTIFICATION OF AMYLOID β PEPTIDES IN PLASMA BY MASS SPECTROMETRY

(71) Applicant: ARACLON BIOTECH, S.L, Saragossa (ES)

(72) Inventors: Jose Antonio Allue Blasco, Saragossa (ES); Maria Leticia Sarasa Coronas, Saragossa (ES)

(73) Assignee: ARACLON BIOTECH, S.L., Saragossa (ES)

( * ) Notice: Subject to any disclaimer, the term of this patent is extended or adjusted under 35 U.S.C. 154(b) by 628 days.

(21) Appl. No.: 17/997,222

(22) PCT Filed: Apr. 29, 2021

(86) PCT No.: PCT/ES2021/070292
§ 371 (c)(1),
(2) Date: Apr. 24, 2023

(87) PCT Pub. No.: WO2021/219917
PCT Pub. Date: Nov. 4, 2021

(65) Prior Publication Data
US 2023/0258651 A1      Aug. 17, 2023

(30) Foreign Application Priority Data
Apr. 29, 2020    (EP) ..................................... 20382352

(51) Int. Cl.
*G01N 33/68*        (2006.01)
*B01D 15/36*        (2006.01)
*C07K 14/47*        (2006.01)

(52) U.S. Cl.
CPC ....... *G01N 33/6848* (2013.01); *B01D 15/363* (2013.01); *C07K 14/4711* (2013.01); *G01N 2333/4709* (2013.01)

(58) Field of Classification Search
None
See application file for complete search history.

(56) References Cited

U.S. PATENT DOCUMENTS 9,588,130 B2    3/2017  Chambers et al.
9,964,545 B2    5/2018  Chambers et al.
(Continued)

FOREIGN PATENT DOCUMENTS

CN       107073131 A      8/2017
CN       109061018        12/2018
(Continued)

OTHER PUBLICATIONS

Galozzi et al., Exp. Rev. Proteomics 12(4): 343-354 (2015).*
(Continued)

*Primary Examiner* — Erin M. Bowers
(74) *Attorney, Agent, or Firm* — Knobbe, Martens Olson & Bear LLP

(57)      ABSTRACT

The present invention relates to a method for preparing a plasma sample comprising amyloid beta peptides for analysis by mass spectrometry, comprising the steps of:
a) contacting said plasma sample with a denaturing agent, b) performing a first solid phase extraction step on the solution obtained in step a) to recover a first eluate, c) performing a second solid phase extraction step on said first eluate obtained in step b) to recover a second eluate, and d) drying said second eluate obtained in step c) and processing it for analysis by mass spectrometry, wherein the solution obtained in step d) comprises intact amyloid beta peptides Aβ40 and Aβ42.

15 Claims, 7 Drawing Sheets

(56) References Cited

U.S. PATENT DOCUMENTS

| | | |
|---|---|---|
| 10,241,117 B2 | 3/2019 | Chambers et al. |
| 2009/0090856 A1 | 4/2009 | Grant et al. |
| 2010/0119478 A1 | 5/2010 | Cynis et al. |
| 2011/0178024 A1 | 7/2011 | Monsonego |
| 2015/0051383 A1 | 2/2015 | Doucette et al. |
| 2017/0010212 A1 | 1/2017 | Gerwert et al. |
| 2017/0089917 A1* | 3/2017 | Tran .................. G01N 33/6848 |

FOREIGN PATENT DOCUMENTS

| | | |
|---|---|---|
| CN | 110230101 | 9/2019 |
| CN | 110501409 | 11/2019 |
| CN | 111024874 A | 4/2020 |
| CN | 114988492 | 9/2022 |
| JP | 2008-519988 A | 6/2008 |
| JP | 2001-514192 A | 9/2021 |
| JP | 7178607 | 11/2022 |
| KR | 2018074089 | 7/2018 |
| KR | 101892481 | 8/2018 |
| RU | 2431143 C2 | 10/2011 |
| WO | WO 2005/056146 A2 | 6/2005 |
| WO | WO 2011/092796 A1 | 4/2011 |
| WO | WO 2013/158277 A1 | 10/2013 |
| WO | WO 2015/025610 A1 | 2/2015 |
| WO | WO 2017/058895 A1 | 4/2017 |
| WO | WO 2018/231415 A1 | 12/2018 |

OTHER PUBLICATIONS

Davidchenko, et al., "Mechanisms of Amyloid Fibril Formation", Biochemistry (Moscow), 79(13): 1515-1527, Jan. 7, 2015.

Lame, et al., "Quantitation of amyloid beta peptides Ab1-38, Ab1-40, and Ab1-42 in human cerebrospinal fluid by ultra-performance liquid chromatography-tandem mass spectrometry", Anal. Biochem. 419 (2011) 133-139. http://dx.doi.org/10.1016/j.ab.2011.08.010.

Office Action issued by the Japanese Patent Office, corresponding to JP Application No. 2022-563460 (English translation provided).

Office Action issued by the Chinese Patent Office, corresponding to CN Application No. 202180030302.1 (English translation provided).

Office Action issued by the Russian Patent Office, corresponding to RU Application No. 2022126759 (English translation provided).

Bateman and Budelier, Biomarkers of Alzheimer Disease, Journal of Applied Laboratory Medicine, Jan. 2020, 194-208.

Fandos et al., Plasma amyloid β 42/40 ratios as biomarkers for amyloid β cerebral deposition in cognitively normal individuals. Alzheimer's Dement, Sep. 12, 2017;8:179-187.

Fukumoto et al., Age but not diagnosis is the main predictor of plasma amyloid beta-protein levels, Arch Neurol. 2003; 60:958-964.

Nakamura et at., High performance plasma amyloid-β biomarkers for Alzheimer's disease, Nature Feb. 8, 2018; 554(7691):249-254.

Ovod et al., Amyloid B concentrations and stable isotope labelling kinetics of human plasma specific to central nervous system amyloidosis, Alzheimer's and Dementia, Oct. 2017; 13(10): 1185.

Pauline Bros et al: "Quantitative detection of amyloid beta peptides by mass spectrometry: state of the art and clinical applications", Clin Chem Lab Med, vol. 53, No. 10, Jan. 1, 2015.

Pérez-Grijalba et al., Plasma Aβ42/40 ratio alone or combined with FDG-PET can accurately predict amyloid-PET positivity: a cross-sectional analysis from the AB255 Study, Alzheimer's Res Ther. 2019;11:96.

Sara Galozzi et al: "Amyloid-β As a biomarker for Alzheimer's disease: quantification methods in body fluids", Exp Rev Proteomics, vol. 12, No. 4, Jul. 4, 2015.

Thomas Lanz et al: "Solid-phase extraction enhances detection of β-amyloid peptides in plasma and enables Abeta quantification following passive immunization with Abeta antibodies", J Neurosci Methods, vol. 169, No. 1, Nov. 22, 2007.

International Search Report issued Jul. 9, 2021; for PCT/ES2021/070292.

Search Report issued by the Russian Patent Office in RU 2022126759/14(058444), which corresponds to the present application (English translation provided).

Official Letter No. 21486 of Dec. 2, 2025, in Colombia Patent Application No. NC2022/0014327.

Bros, et al., Quantitative detection of amyloid-β peptides by mass spectrometry: State of the art and clinical applications. In Clinical Chemistry and Laboratory Medicine (vol. 53, Issue 10, pp. 1483-1493). Walter de Gruyter GmbH., 2015.

Fong, et al., "Development and validation of a high throughput double solid phase extraction-liquid chromatography-tandem mass spectrometry method for the determination of tetrodotoxin in human urine and plasma", Jan. 15, 2011.

Ventura, et al., Ionic-Liquid-Mediated Extraction and Separation Processes for Bioactive Compounds: Past, Present, and Future Trends. In Chemical Reviews (vol. 117, Issue 10, pp. 6984-7052). American Chemical Society 2017.

* cited by examiner

AUC=0.8365

METHODS FOR QUANTIFICATION OF AMYLOID β PEPTIDES IN PLASMA BY MASS SPECTROMETRY

The present invention relates to the field of medicine and veterinary science in the diagnosis of amyloid diseases, and in particular, to analytical methods for the preparation of plasma samples for detection and quantification of amyloid Aβ40 and Aβ42 peptides by mass spectrometry.

BACKGROUND

Alzheimer's disease (AD) is a leading cause of dementia, characterized by progressive degenerative disease of the central nervous system, which affects 17% of people of age between 75-84 and 32% of those over 85 (Bateman and Budelier, *Biomarkers of Alzheimer Disease, Journal of Applied Laboratory Medicine*, January 2020, 194-208). AD is characterized by progressive appearance in the brain of the patients of amyloid plaques having central cores of amyloid deposits formed mainly by fibrils of a 40-42 amino acids peptides. Said amyloid deposits are formed after proteolytic processing of the amyloid precursor protein (APP), resulting in the generation of insoluble Aβ peptides, mostly Aβ1-40 (Aβ40) and Aβ1-42 (Aβ42). In healthy patients, these peptides are cleared into the cerebrospinal fluid (CSF) or are transported into the blood across the blood-brain barrier. However, overproduction or reduction in clearance of amyloid peptides results in formation of the amyloid plaques that are characteristic of AD. These plaques primarily contain Aβ42 and act as a "sink" for the peptide, reducing Aβ42 concentrations in both CSF and blood.

Thus, Aβ42/Aβ40 concentration ratio is currently being used as a brain amyloidosis biomarker in the early stages of Alzheimer's disease for inclusion in clinical trials. Aβ42 and Aβ40 can be measured by either mass spectrometry (MS) or immunoassay, being most of the methods currently available conducted in cerebrospinal fluid (CSF), wherein lower Aβ42 concentrations are found when amyloid plaques are present (Bateman and Budelier, *Biomarkers of Alzheimer Disease, Journal of Applied Laboratory Medicine*, January 2020, 194-208). However, CSF collection is quite invasive and requires professional medical skills, which is not the most convenient for large screening studies. Therefore, methods to quantify Aβ42 and Aβ40 in plasma are of much interest for diagnosing individuals with or without symptoms (Fandos et al., *Plasma amyloid β42/40 ratios as biomarkers for amyloid β cerebral deposition in cognitively normal individuals. Alzheimer's Dement*, 2017 Sep. 12; 8:179-187).

Nevertheless, measuring concentration of Aβ42 and Aβ40 in plasma also entails difficulties. Firstly, blood is a very complex matrix comprising high amounts of numerous proteins which results in a total protein content of 60-fold greater in plasma versus CSF. Secondly, the concentration of Aβ42 and Aβ40 is lower compared to CSF due to transport from the central nervous system into the venous blood. In addition, the difference in Aβ42 concentration in plasma between amyloid-positive and amyloid-negative individuals is smaller than in CSF (Bateman and Budelier, *Biomarkers of Alzheimer Disease, Journal of Applied Laboratory Medicine*, January 2020, 194-208). For said reasons, analysis of amyloid beta peptides in plasma is more challenging than in CSF and therefore, more sensitive and accurate methods are required.

Prior studies using enzyme-linked immunosorbent assay (ELISA) to measure the concentration of amyloid beta peptide in plasma have shown contradictory results regarding Aβ42/Aβ40 concentration ratio measurements in AD patients and healthy controls (Fukumoto et al., Age but not diagnosis is the main predictor of plasma amyloid beta-protein levels, Arch Neurol. 2003; 60:958-964; Pérez-Grijalba et al., *Plasma Aβ42/40 ratio alone or combined with FDG-PET can accurately predict amyloid-PET positivity: a cross-sectional analysis from the AB255 Study, Alzheimer's Res Ther.* 2019; 11:96). In fact, mean differences between groups (i.e. healthy controls vs mild cognitive impairment individuals) are as low as 10-15%, the same magnitude of the acceptable variability for accuracy and precision for analytical methods. This implies that in order to detect such a low difference between groups, the variability of the analytical methods has to be much lower than 15%.

On the other hand, available mass spectrometry (MS) methods have been demonstrated to be more sensitive and precise than immunoassays. Currently, there are two MS-based analytical methods for Aβ40 and Aβ42 determination in human plasma known in the art. The first one was published in 2017 by the group of Randall Bateman (Ovod et al., *Amyloid B concentrations and stable isotope labelling kinetics of human plasma specific to central nervous system amyloidosis, Alzheimer's and Dementia*, 2017 October; 13(10): 1185). This method combines preparation of the sample by immunoprecipitation and Lys-N digestion with nanoLC-MS/MS. The second method was published in 2018 by the group of Akinori Nakamura (Nakamura et at., *High performance plasma amyloid-β biomarkers for Alzheimer's disease, Nature* 2018 Feb. 8; 554(7691):249-254) and combines preparation of the sample by double immunoprecipitation with MALDI-TOF/MS.

However, both methods are time and resource consuming, since they require the use of expensive antibodies during immunoprecipitation. In addition, the method of Bateman further requires analyte enzymatic digestion of the sample, which results in detection of a mixture of N-truncated Aβ species rather than intact Aβ peptides.

Accordingly, there remains a need in the art for sensitive and reproducible methods for detection and quantification of amyloid beta peptides in plasma samples that could be applied to large screening studies.

The inventors of the present invention, after extensive and thorough experimentation, have surprisingly discovered a new method for the preparation of plasma samples comprising amyloid peptides that allows for the accurate quantification of intact amyloid peptides Aβ40 and Aβ42 by mass-spectrometry. Thus, this new method reduces variability in the measurement of Aβ42/Aβ40 ratios to values lower than the actual difference between healthy controls and mild cognitive impairment individuals.

In addition, the method of the present invention is carried out without using immunoprecipitation or digestion of the sample, which are essential steps of the methods known in the art, and therefore, it provides simpler and faster sample preparation, reducing cost and time requirements in comparison with the current available methods.

Finally, the method of the present invention comply with the current FDA's recommendations for bioanalytical method validation and therefore, can be applied to diagnosing and/or distinguishing between different stages of a neurodegenerative disease, for example, Alzheimer's disease.

SUMMARY

In one aspect, the present invention refers to a method for preparing a plasma sample comprising amyloid beta peptides for analysis by mass spectrometry, characterized in that it comprises the steps of:

a) Contacting said plasma sample with a denaturing agent, b) Performing a first solid phase extraction step on the solution obtained in step a) to recover a first eluate, c) Performing a second solid phase extraction step on said first eluate obtained in step b) to recover a second eluate, and d) Drying said second eluate obtained in step c) and processing it for analysis by mass spectrometry, wherein the sample obtained from step d) comprises intact amyloid beta peptides Aβ40 and Aβ42.

In one embodiment of said method the second solid phase extraction step is a cation exchange solid phase extraction.

In another embodiment, the cation exchange solid phase extraction is a strong, weak or Mixed Mode Reverse Phase-Cation Exchange.

In another embodiment, the second solid phase extraction step is an anion exchange solid phase extraction.

In another embodiment, the second anion exchange solid phase extraction is a strong, weak or Mixed Mode Reverse Phase-Anion Exchange.

In another embodiment, the plasma sample is contacted with an acidic denaturing agent in step a) to obtain a solution having a pH of less than or equal to 4.5.

In another embodiment, the acidic denaturing agent is a solution of formic acid in water at a concentration between 40% and 70% (v/v).

In another embodiment, the first solid phase extraction step is a reverse-phase solid phase extraction.

In another embodiment, the first and second solid phase extraction steps comprise each of them at least two wash steps characterized in that the first wash steps of the first and second solid phase extraction steps are carried out with a solution comprising an acid and the second wash steps of the first and second solid phase extraction steps are carried out with a solution comprising a water miscible polar organic solvent.

In another embodiment, the solution comprising an acid of the first wash steps is different than the solution comprising an acid of the second wash steps.

In another embodiment, the solution comprising an acid of the first wash steps in the same than the solution comprising an acid of the second wash steps.

In another embodiment, the first solid phase extraction step is a cation exchange solid phase extraction.

In another embodiment, the first cation exchange solid phase extraction is a strong, weak or Mixed Mode Reverse Phase-Cation Exchange.

In another embodiment, the first and second solid phase extraction steps comprise each of them at least two wash steps characterized in that the first wash step of the first solid phase extraction is carried out with a solution comprising an acid and the first wash step of the second solid phase extraction is carried out with a solution comprising a base, and the second wash steps of the first and second solid phase extraction steps are carried out with a solution comprising a water miscible polar organic solvent.

In another embodiment, the plasma sample is contacted with a basic denaturing agent in step a) to obtain a solution having a pH of more than or equal to about 11.

In another embodiment, the basic denaturing agent is a solution of ammonium hydroxide in water at a concentration between 5% and 50% (v/v).

In another embodiment, the first solid phase extraction step is an anion exchange solid phase extraction.

In another embodiment, the first anion exchange solid phase extraction is a strong, weak or Mixed Mode reverse Phase-Anion Exchange.

In another embodiment, the first and second solid phase extraction steps comprise each of them at least two wash steps characterized in that the first wash step of the first solid phase extraction is carried out with a solution comprising an acid and the first wash step of the second solid phase extraction is carried out with a solution comprising a base, and the second wash steps of the first and second solid phase extraction steps are carried out with a solution comprising a water miscible polar organic solvent.

In yet another embodiment, the solution for processing the second eluate for analysis by mass spectrometry is an aqueous solution comprising a surfactant and a reducing agent. In a preferred embodiment, said solution of step d) for processing the dried eluate is an aqueous solution comprising Triton X-100 at a concentration between 0.01% and 0.8% (v/v) and tris-carboxyethylphosphine at a concentration between 0.1% and 0.2% (w/v).

In another embodiment, said solution of step d) for processing the dried eluate is an aqueous solution comprising a surfactant, a reducing agent, a water miscible polar organic solvent and an acid. In a preferred embodiment, said solution of step d) for processing the dried eluate is an aqueous solution comprising Triton X-100 at a concentration between 0.01% and 0.8% (v/v), tris-carboxyethylphosphine at a concentration between 0.1% and 0.2% (w/v), acetonitrile at a concentration between 3% and 7% (v/v), dimethylformamide at a concentration between 0.1% and 3% (v/v) and trifluoroacetic acid (TFA) at a concentration between 0.1% and 3% (v/v).

In some embodiments of the present invention, the plasma sample is a human plasma sample. In other embodiments, the volume of plasma sample used in step a) of the method of the present invention is between 100 μL and 400 μL.

In some embodiments of the present invention, the method for preparing a plasma sample comprising amyloid beta peptides for analysis by mass spectrometry does not comprise immunoprecipitation or digestion of the plasma sample prior the mass spectrometry analysis.

In a second aspect, the present invention refers to a method for quantification of intact amyloid beta peptides Aβ40 and Aβ42 in a plasma sample by mass spectrometry, characterized in that it comprises the steps a) to d) of the method for preparing a plasma sample as described herein and further comprises the steps of:

i) Performing a liquid-chromatography step on the solution obtained in step d), to separate the analytes of interest, ii) Subjecting the analytes separated in step i) to ionization to generate one or more charged species;

iii) Separating said one or more charged species according to their ion mobility, iv) Detecting said one or more charged species separated in step iii) and measuring their abundance by mass spectrometry; and v) Determining the amount or concentration of intact amyloid beta peptides Aβ40 and/or Aβ42 in the plasma sample by comparison of the abundances of the one or more charged species measured in step iv) with a standard curve.

In some embodiments, said method for quantification of intact amyloid beta peptides Aβ40 and Aβ42 in a plasma sample by mass spectrometry is characterized in that the liquid-chromatography is micro-liquid chromatography (micro-HPLC), the ionization is electrospray ionization (ESI), the separation of the one or more charged species is carried out by differential mobility spectrometry (DMS) and the mass spectrometry technique for detecting and measuring the abundances of the separated one or more charged species is multiple reaction monitoring (MRM) in a triple quadrupole instrument.

In other embodiments of the present invention, the standard curve used in said method for quantification of intact amyloid beta peptides Aβ40 and Aβ42 in a plasma sample by mass spectrometry is prepared with human plasma.

In a third aspect, the present invention refers to an aqueous solution for processing a dried eluate to be analysed by mass spectrometry comprising Triton X-100 at a concentration between 0.01% and 0.8% (v/v), tris-carboxyethylphosphine at a concentration between 0.1% and 0.2% (w/v), acetonitrile at a concentration between 3% and 7% (v/v), dimethylformamide at a concentration between 0.1% and 3% (v/v) and trifluoroacetic acid (TFA) at a concentration between 0.1% and 3% (v/v).

DETAILED DESCRIPTION

Figure 1:
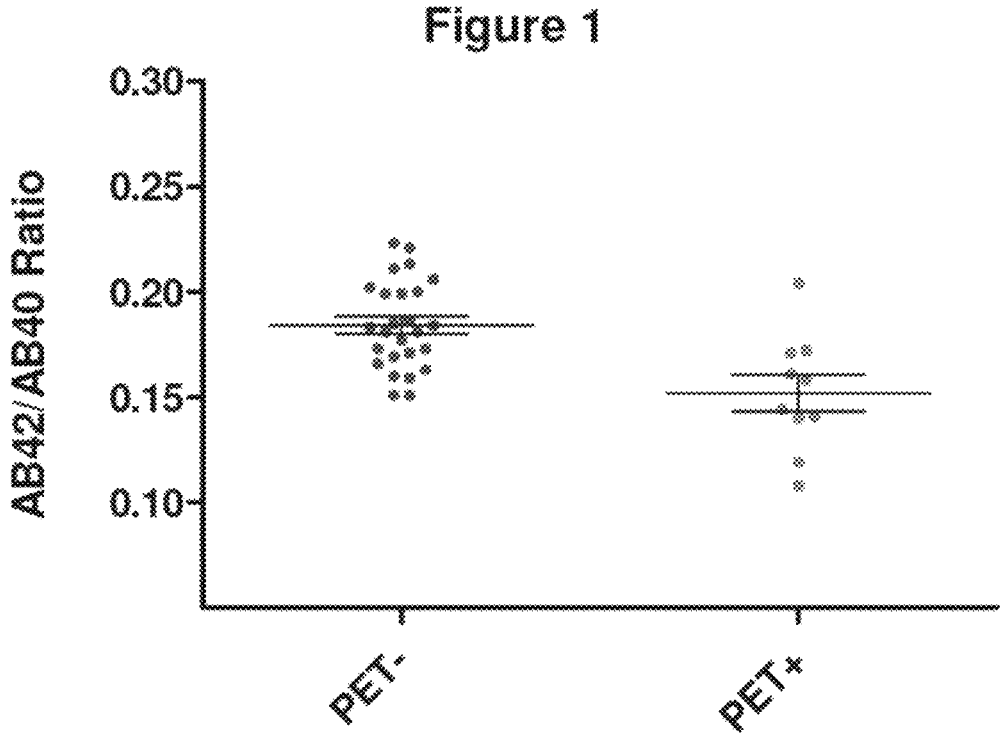
FIG. 1 shows a graph representing the Aβ42/Aβ40 ratios corresponding to samples of 36 individuals (PET negative or PET positive) quantified by the methods of the present invention.

The following description is merely intended to illustrate various embodiments of the present invention. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

As used in the present invention, the singular forms "a," "an" and "the" include plural references unless the content clearly dictates otherwise.

Throughout this specification and the claims, unless the context requires otherwise, the word "comprise", or variations such as "comprises" or "comprising", will be understood to imply the inclusion of a stated element or group of elements but not the exclusion of any other element or group of elements.

The terms "analyte", "specie", "sample", "component", "chemical" and "ion" may all be used herein to refer to a substance to be analysed, identified and quantified by the methods of the present invention.

The term "solid-phase extraction" or "SPE", as used herein, refers to a process by which a mixture is separated into components. The components are dissolved and/or suspended in solution ("sample solution") and are separated from each other by their different affinities for a solid through which the solution is passed ("stationary phase"). In some instances, as the sample solution passes through the stationary phase, undesired components of the sample solution may be retained by the stationary phase (i.e., the analyte in the sample solution is purified). In other instances, desired components may be retained by the stationary phase (i.e., the analyte of interest is retained in the stationary phase), and a second mobile phase is used to elute the retained analyte of the stationary phase for further processing or analysis. The "stationary phase" is commonly contained in a "cartridge", a "tip" or a "column", which can be gathered in multi-well plates, which are particularly convenient for large screening studies. Solid phase extraction cartridges, columns, tips and multi-well plates are commercially available, or may be prepared according to methods known in the art.

The term "purification" refers to a procedure that enriches the amount of one or more analytes of interest relative to other components in the sample that may interfere with detection of the analyte of interest. As used herein, the term "purification" does not refer to removing all material from the sample other than the analyte(s) of interest.

"Immunoprecipitation" refers to a purification procedure that utilizes antibodies, including polyclonal or monoclonal antibodies, to enrich a sample in the one or more analytes of interest.

The term "digestion", as used herein, refers generally to any suitable method for degrading or cleaving a polypeptide or protein, including, for example, the use of cellular enzymes (proteases) and intramolecular digestion.

The terms "mass spectrometry" or "MS", as used herein, refer to an analytical technique to measure mass-to-charge ratio of a particular analyte. MS is used broadly to include all components and systems that may be used to detect and identify analytes using their mass-to-charge ratio. MS technology generally includes ionizing the analytes (though they can previously be ionized in solution) to form charged analytes, transferring these charged analytes to the gas phase, determining the mass-to-charge ratio and calculating the relative or absolute abundances. The analytes may be ionized and detected by any suitable means.

The term "chromatography" refers to a process by which a mixture carried by a liquid or gas is separated into components that elute at different retention times as a result of differential distribution of the chemical entities as they flow through a stationary phase. Thus, "liquid chromatography" (LC) or "high performance liquid chromatography" (HPLC) refers to the selective separation of one or more components of a fluid solution as the fluid moves through a column. The separation results from the partitioning of the components of the mixture between one or more stationary phases and the mobile phase. Examples of LC or HPLC include normal phase liquid chromatography (NPLC), reversed phase liquid chromatography (RPLC), high turbulence liquid chromatography (HTLC), hydrophilic interaction chromatography (HILIC), ion exchange chromatography (IEC), size exclusion chromatography (SEC), hydrophobic interaction chromatography (HIC), electrostatic repulsion liquid chromatography (ERLIC), and multidimensional liquid chromatography.

The term "micro-HPLC" or "micro-LC" refers to high performance liquid chromatography (HPLC) employing microflow rates (i.e. 1-25 µl/min) and capillary columns (150-500 µm internal diameter).

The terms "ionization" or "ionizing", as used herein, refer to a process by which an analyte ion having a net electrical charge equal to one or more charge units is generated. Negative ions have a net negative charge, and positive ions have a net positive charge. Non-limiting examples of ionization includes electron ionization, chemical ionization, electrospray ionization (ESI), atmospheric pressure photoionization (APPI), matrix assisted laser desorption ionization (MALDI), atmospheric pressure chemical ionization (APCI), among others.

"Electrospray ionization" or "ESI" refers to an ionization method in which an analyte of interest is transferred as an ion to the gas phase, wherein a sample solution containing the analyte of interest is sprayed into an electric field to form charged droplets.

The term "ion-mobility spectrometry (IMS)" refers to an analytical technique used to separate and identify ionized molecules in the gas phase based on their mobility in a carrier buffer gas. The term "differential mobility spectrometry (DMS)" refers to a particular type of IMS that consists of separation of the ionized molecules based on the difference between ion mobility in high and low electric fields, in gases at, or near, atmospheric pressure.

The term "multiple reaction monitoring (MRM)", also called "selected reaction monitoring (SRM)" refers to a scan mode in tandem MS in which two (or more) analysing devices (i.e. quadrupoles) are adjusted to monitor one or more chosen parent-product pairs of the analytes of interest.

The terms "tandem mass spectrometry" or "MS/MS" refer to mass spectrometry in which multiple stages of mass analysis are performed, wherein the multiple stages are separated in time or in space. For example, tandem mass spectrometry in time can involve one mass analyser (e.g., an ion trap), in which particular ions are first trapped, isolated, and fragmented, and then fragments are analysed in the same mass analyser. Tandem mass spectrometry in space involves more than one analyser. The analysers are separated by one or more reaction regions (i.e. a collision cell filled with a gas as argon, xenon, nitrogen, helium) where analyte dissociation takes place. Finally, fragment ions are filtered in the final analyser and then detected. In general, two analysers are used. These may, or may not, be of the same type.

As used herein, the term "ROC" means "receiver operating characteristic". A ROC analysis may be used to evaluate the diagnostic performance, or predictive ability, of a test or a method of analysis. A ROC graph is a plot of sensitivity and specificity of a test at various thresholds or cut-off values. Each point on a ROC curve represents the sensitivity and its respective specificity. A threshold value can be selected based on an ROC curve to identify a point where sensitivity and specificity both have acceptable values, and this value can be used in applying the test for diagnostic purposes. If only specificity is optimized, then the test will be less likely to generate a false positive (diagnosis of the disease in more subjects who do not have the disease) at the cost of an increased likelihood that some cases of disease will not be identified (e.g. false negatives). If only sensitivity is optimized, then the test will be more likely to identify most or all of the subjects with the disease, but will also diagnose the disease in more subjects who do not have the disease (e.g. false positives). A user is able to modify the parameters, and therefore select a ROC threshold value suitable for a given clinical situation, in ways that will be readily understood by those skilled in the art.

The term "area under the curve (AUC) value", quantifies the overall ability of the test to discriminate between different sample properties, in this case to discriminate between those subjects with Aβ amyloidosis (i.e. amyloid positive) and those without Aβ amyloidosis (i.e. amyloid negative). A test that is no better at identifying true positives than random chance will generate a ROC curve with an AUC of 0.5. A test having perfect specificity and sensitivity (i.e., generating no false positives and no false negatives) will have an AUC of 1.00.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used and will be apparent to those of skill in the art.

Each embodiment in this specification is to be applied mutatis mutandis to every other embodiment unless expressly stated otherwise.

The present invention relates to a method for preparing a plasma sample comprising amyloid beta peptides for analysis by mass spectrometry.

Amyloid beta peptides (also referred to as Aβ or Abeta peptides) are peptides resulting from proteolytic processing of the amyloid precursor protein (APP). As used herein, the term "amyloid beta" refers to total amyloid beta (Aβ) protein, Aβ40, Aβ42, or another Aβ isoform. In some embodiments, a sample may comprise Aβ40. In other embodiments, a sample may comprise Aβ42. In preferred embodiments, a sample may comprise Aβ40 and Aβ42.

As used herein, the term "intact" amyloid beta refers to full length peptides that have not been subjected to chemical/enzymatic cleavage or any other peptide modification. In the precise case of Aβ40 and Aβ42 peptides, intact amyloid beta peptide Aβ42 refers to a 42 amino acid peptide which corresponds to amino acids 672 to 713 of human APP isoform 770 (canonical, accession number in UniProtKB P05067) and intact amyloid beta peptide Aβ40 refers to a 40 amino acid peptide which corresponds to amino acids 672 to 711 of human APP isoform 770 (canonical, accession number in UniProtKB P05067).

In some embodiments, a sample is a plasma sample derived from a subject. Suitable subjects include humans or any other mammal, livestock animals (such as pigs, cows, horses, goats, sheep, llamas and alpacas), companion animals (such as dogs, cats, rabbits, and birds), lab animals (such as rodent, e.g. a mouse, a rat, a guinea pig), or zoological animals. In preferred embodiments, the subject is a mammal. In more preferred embodiments, the subject is human.

The plasma sample may be used "as it is", or a protein fraction may be isolated from the plasma sample using standard techniques. For instance, a plasma sample may be concentrated, diluted, or extracted. Suitable extraction techniques may include surfactants, acids, bases, organic solvents, or other methods known in the art. In some embodiments, raw samples can be pre-treated in order to reduce the complexity of the matrix. In some embodiments, these pre-treatments are techniques well-known by the skilled person, such as liquid-liquid extraction or protein precipitation, but other techniques known by the skilled person are not excluded. In some embodiments, a plasma sample is preferred. In a more preferred embodiment, the plasma sample is a human plasma sample.

In a first aspect, the present invention relates to a method for preparing a plasma sample comprising amyloid beta peptides for analysis by mass spectrometry. Said method comprises the following steps:

a) Contacting said plasma sample with a denaturing agent, b) Performing a first solid phase extraction step on the solution obtained in step a) to recover a first eluate, c) Performing a second solid phase extraction step on said first eluate obtained in step b) to recover a second eluate, and d) Drying said second eluate obtained in step c) and processing it for analysis by mass spectrometry, wherein the sample obtained from step d) comprises intact amyloid beta peptides $A\beta40$ and $A\beta42$.

The term "processing" in step d) refers to adequate the sample for analysis by mass spectrometry and includes, for example, adequate the sample to liquid chromatography coupled to mass spectrometry.

In some embodiments, the plasma sample comprising amyloid beta peptides is contacted with an acidic denaturing agent. In more preferred embodiments, the acidic denaturing agent is an organic acid. In yet more preferred embodiments, the organic acid is a carboxylic acid. In yet more preferred embodiments, the carboxylic acid is a mono-, di-, or tricarboxylic acid. The mono-, di-, or tricarboxylic acid may have a pKa of about $\leq6$, for example about $\leq5$, such as about $\leq4$. The mono-, di- or tricarboxylic acid may have a pKa of about $\leq4$. In a preferred embodiment, the mono-, di- or tricarboxylic acid is C1-C10 haloalkyl, C1-C10 alkyl, and combinations thereof. For example, the carboxylic acid may be selected from C1-C5 haloalkyl monocarboxylic acid, a C1-C5 alkyl monocarboxylic acid, and combinations thereof. In yet more preferred embodiments, the carboxylic acid is formic acid.

All pKa values disclosed herein are as measured in water at 25° C., and 1 atm pressure.

Thus, in some embodiments, the acidic denaturing agent is formic acid. In a yet more preferred embodiment the acidic denaturing agent is a solution of formic acid in water comprising between 40% and 70% (v/v) of formic acid. In a preferred embodiment, the solution of formic acid comprises between 45% and 60% (v/v) of formic acid in water. In a more preferred embodiment, the solution of formic acid comprises about 50% (v/v) of formic acid in water.

In some preferred embodiments, the plasma sample comprising amyloid beta peptides is contacted with the acidic denaturing agent to obtain a solution having a pH of less than or equal to about 4.5. In more preferred embodiments, pH of the solution may be between about 0.1 and about 4.5. For example, the pH of the solution may be between about 0.4 and about 3. The pH of the solution may be between about 0.5 and 2, for example between about 0.8 and 1.5. In more preferred embodiment, the solution obtained after contacting the plasma sample with the acidic denaturing agent has a pH between 1 and 1.4, more preferably between 1.1 and 1.3, more preferably about 1.2.

The volume of the acidic denaturing agent used in the methods of the present invention depends on the volume of the plasma sample used and the pH of said acidic denaturing agent. The skilled person is able to determine the volume of the acidic denaturing agent to obtain a solution having a specific pH with simple calculations. In some preferred embodiments of the present invention, the acidic denaturing agent is formic acid at a concentration between 40% and 70% (v/v) in water. In more preferred embodiments of the present invention, a volume of plasma sample between 100 µl and 400 µl is contacted with a volume between 200 µl and 800 µl of formic acid at a concentration between 40% and 70% (v/v) in water.

The use of a formic acid as denaturing agent for denaturing the plasma sample of the present invention provides for several advantages, such as disruption of many $A\beta$-plasma protein interactions (i.e. IgGs) while keeping $A\beta$ peptides in solution (no precipitation occurs).

In some embodiments, the plasma sample comprising amyloid beta peptides is contacted with a basic denaturing agent. In more preferred embodiments, the basic denaturing agent is selected from the group consisting of water soluble hydroxides, carbonates, oxides and combinations thereof. For example, the base may be a water soluble hydroxide. Suitable hydroxides include inorganic hydroxides, organic hydroxides and combinations thereof. In a preferred embodiment, the base is ammonium hydroxide. In a yet more preferred embodiment the basic denaturing agent is a solution of ammonium hydroxide in water comprising between 15% and 40% (v/v) of ammonium hydroxide. In a preferred embodiment, the solution of basic agent comprises between 20% and 50% (v/v) of ammonium hydroxide in water. In a more preferred embodiment, the solution of basic agent comprises about 25% (v/v) of ammonium hydroxide in water.

In some preferred embodiments, the plasma sample comprising amyloid beta peptides is contacted with a basic denaturing agent to obtain a solution having a pH of more than or equal to about 11. In more preferred embodiments, pH of the solution may be between about 11 and about 13. For example, the pH of the solution may be between about 11 and about 12. The pH of the solution may be between about 11 and 11.5, most preferably about 11.3.

The volume of the basic denaturing agent used in the methods of the present invention depends on the volume of the plasma sample used and the pH of said basic denaturing agent. The skilled person is able to determine the volume of the basic denaturing agent to obtain a solution having a specific pH with simple calculations. In some preferred embodiments of the present invention, the basic denaturing agent is ammonium hydroxide at a concentration between 15% and 40% (v/v) in water. In more preferred embodiments of the present invention, a volume of plasma sample between 100 µl and 400 µl is contacted with a volume between 200 µl and 800 µl of ammonium hydroxide at a concentration between 15% and 40% (v/v) in water.

The use of a ammonium hydroxide as denaturing agent for denaturing the plasma sample of the present invention provides for several advantages, such as disruption of many $A\beta$-plasma protein interactions (i.e. IgGs) while keeping $A\beta$ peptides in solution (no precipitation occurs).

After denaturing the sample, amyloid beta peptides are separated from other components of the sample by solid phase extraction (SPE).

Several types of SPE are known in the art. They can be classified depending on the chemical properties of the stationary phases employed. Thus, in normal phase SPE, the stationary phase is more polar than the mobile phase, such as combination of silica gel or alumina as stationary phases with mobile phases of less polar eluents (i.e. hexane). On the contrary, reversed phase SPE uses low polarity packings, as octadecylsilane or octylsilane, bonded to silica or polymeric beads and mobile phases are usually mixtures of waters and organic miscible solvents and modifiers. During ion-exchange SPE, on the other hand, the components are separated based on electrostatic interactions between the components and the positively or negatively charged group of the stationary phase. Thus, ion-exchange SPE includes anion exchange SPE, in which the stationary phase comprises positively charged groups which interact and retain negatively charged anions, such as acids, and cation exchange SPE, in which the stationary phase comprise negatively charged groups which interact and retain positively charged cations, such as bases. Strong cation exchange sorbents contain aliphatic sulfonic acid groups that are always negatively charged in aqueous solution, and weak cation exchange sorbents contain aliphatic carboxylic acids, which are charged when the pH is above 5. It is also possible to combine multiple retention mechanisms in the same cartridge, what is known as mixed-mode SPE, which often combine reversed phase and ion-exchange cartridges. Thus, Mixed-Mode Reversed Phase-Anion Exchange and Mixed-Mode Reversed Phase-Cation Exchange are known SPE in the art.

The purpose of solid phase extraction in the method of the present invention is to separate and discard the undesired components of the plasma sample in order to purify and concentrate the sample in the amyloid beta peptides of interest.

In some embodiments, the method of the present invention comprises performing a first solid phase extraction step on the solution obtained after contacting the sample with the denaturing agent. In preferred embodiments, the method of the present invention comprises performing a second solid phase extraction step after said first solid phase extraction step. Therefore, in some embodiments the method for preparing a sample comprising amyloid beta peptides for analysis by mass spectrometry of the present invention comprises two consecutive solid phase extraction steps.

In some embodiments, the first and second solid phase extraction steps of the method for preparing a sample comprising amyloid beta peptides of the present invention can be of any type known by the skilled person.

In some embodiments, the first solid phase extraction step is a reversed-phase SPE. In some embodiments, the first solid phase extraction step is a cation exchange SPE. In some embodiments, the first solid phase extraction step is an anion exchange SPE. In some embodiments, the cation exchange SPE is a strong, weak or mixed-mode reversed phase-cation exchange. In some embodiments, the anion exchange SPE is a strong, weak or mixed-mode reversed phase-anion exchange.

In some embodiments, the second solid phase extraction step is a reversed-phase SPE. In some embodiments, the second solid phase extraction step is a cation exchange SPE. In some embodiments, the second solid phase extraction step is an anion exchange SPE. In some embodiments, the cation exchange SPE is a strong, weak or mixed-mode reversed phase-cation exchange. In some embodiments, the anion exchange SPE is a strong, weak or mixed-mode reversed phase-anion exchange.

In some embodiments, the first solid phase extraction step is a reversed-phase SPE and the second solid phase extraction step is a cation exchange SPE, more preferably said cation exchange SPE is a strong, weak or mixed-mode reversed phase-cation exchange.

In some embodiments, the first solid phase extraction step is a reversed-phase SPE and the second solid phase extraction step is an anion exchange SPE, more preferably said anion exchange SPE is a strong, weak or mixed-mode reversed phase-anion exchange.

In some embodiments, the first solid phase extraction step is a cation exchange SPE, more preferably said cation exchange SPE is a strong, weak or mixed-mode reversed phase-cation exchange, and the second solid phase extraction step is an anion exchange SPE, more preferably said anion exchange SPE is a strong, weak or mixed-mode reversed phase-anion exchange.

In some embodiments, the first solid phase extraction step is an anion exchange SPE, more preferably said anion exchange SPE is a strong, weak or mixed-mode reversed phase-anion exchange, and the second solid phase extraction step is cation exchange SPE, more preferably said cation exchange SPE is a strong, weak or mixed-mode reversed phase-cation exchange.

In some preferred embodiments of the method for preparing a plasma sample comprising amyloid beta peptide for analysis by mass spectrometry of the present invention, the plasma sample is contacted with an acidic denaturing agent as disclosed herewith before a first and a second SPE are performed, wherein the first SPE is a reversed-phase SPE and the second solid phase extraction step is a cation exchange SPE.

In some preferred embodiments of the method for preparing a plasma sample comprising amyloid beta peptide for analysis by mass spectrometry of the present invention, the plasma sample is contacted with an acidic denaturing agent as disclosed herewith before a first and a second SPE are performed, wherein the first SPE is a reversed-phase SPE and the second solid phase extraction step is an anion exchange SPE.

In some preferred embodiments of the method for preparing a plasma sample comprising amyloid beta peptide for analysis by mass spectrometry of the present invention, the plasma sample is contacted with an acidic denaturing agent as disclosed herewith before a first and a second SPE are performed, wherein the first SPE is a cation exchange SPE and the second solid phase extraction step is an anion exchange SPE.

In some preferred embodiments of the method for preparing a plasma sample comprising amyloid beta peptide for analysis by mass spectrometry of the present invention, the plasma sample is contacted with a basic denaturing agent as disclosed herewith before a first and a second SPE are performed, wherein the first SPE is an anion exchange SPE and the second solid phase extraction step is cation exchange SPE.

The specific combination of the two consecutive SPE steps as described herein after denaturing the proteins in a plasma sample comprising amyloid peptides according to the method of the present invention allows for purification of intact Aβ40 and Aβ42 peptides, which can be further analysed by mass spectrometry without any further purification step being required.

The protocol for carrying out the first and second SPE steps of the present invention comprises conditioning and equilibration of the stationary phase, loading the sample into the column or cartridge, at least one wash step and at least one elution step. Said steps are well known by the skilled person and the specific conditions for each step are also known in the art.

In one embodiment of the present invention, the protocol for carrying out the first and second SPE steps of the present invention are those known in the art. In another embodiment of the present invention, the first and second SPE steps comprise at least one wash step to remove undesired components from the sample. In a preferred embodiment of the present invention each of the first and second SPE steps comprise at least two wash steps.

Suitable wash solutions are known in the art. In some embodiments, the wash solution for the SPE steps of the methods of the present invention is a solution of an acid, such as an organic acid, preferably acetic acid, formic acid or trifluoroacetic acid (TFA). In other embodiments, the wash solution for the SPE steps of the methods of the present invention is a solution of water and a water miscible organic solvent. For example, the water miscible organic solvent may be a polar aprotic, or a protic organic solvent. Non-limiting examples of classes of water miscible organic solvents include, without limitation, esters, nitriles, carboxylic acids, amides, aldehydes, ketones and combinations thereof. It will be understood by those of skill in the art that not every member of the above indicated classes is water miscible, however, those of skill in the art can readily determine the members of a particular class that are water miscible. In yet more preferred embodiments, the water miscible organic solvent is acetonitrile, dimethylformamide, or combinations thereof. In a particularly preferred embodiment, the water miscible organic solvent of the wash solution for the SPE steps of the method of the present invention is acetonitrile. In other embodiments, the wash solution for the SPE steps of the methods of the present invention is a solution of a base, such as water soluble hydroxides, carbonates, oxides and combinations thereof. In a preferred embodiment, the wash solution for the SPE steps of the methods of the present invention is a solution of ammonium hydroxide.

In some preferred embodiments, the wash solution for a first wash is trifluoroacetic acid (TFA). The concentration of TFA that can be used for a first wash during the SPE steps of the present invention is between 0.01% and 10% (v/v) TFA in water. In another preferred embodiment, the wash solution is between 0.05% and 1% (v/v) TFA in water. In a yet more preferred embodiment, the wash solution is about 0.1% (v/v) TFA in water. In a preferred embodiment, the wash solution for a first wash during the first SPE step of the present invention is between 0.05% and 1% (v/v) TFA in water, more preferably about 0.1% TFA in water.

In some preferred embodiments, the wash solution for a first wash is formic acid. The concentration of formic acid that can be used for a first wash during the SPE steps of the present invention is between 15% and 35% (v/v) formic acid in water. In a preferred embodiment, the wash solution is between 20% and 30% (v/v) formic acid in water. In a more preferred embodiment, the wash solution is about 25% (v/v) formic acid in water. In another preferred embodiment, the wash solution for a first wash during the second SPE step of the present invention is between 20% and 30% (v/v) formic acid in water, more preferably about 25% (v/v) formic acid in water.

In some preferred embodiments, the wash solution for a first wash is a solution of ammonium hydroxide. The concentration of ammonium hydroxide that can be used for a first wash during the SPE steps of the present invention is between 2-50% (v/v) ammonium hydroxide in water. In a preferred embodiment, the wash solution is between 2% and 30% (v/v) ammonium hydroxide in water. In a more preferred embodiment, the wash solution is about 10% (v/v) ammonium hydroxide in water. In another preferred embodiment, the wash solution for a first wash during the second SPE step of the present invention is between 5% and 30% (v/v) ammonium hydroxide in water, more preferably about 10% (v/v) ammonium hydroxide in water.

In some preferred embodiments, the wash solution for a second wash is acetonitrile. The concentration of acetonitrile that can be used for a second wash during the SPE steps of the present invention is between 5% and 80% (v/v) acetonitrile in water. In a preferred embodiment, the wash solution is between 10% and 60% (v/v) acetonitrile in water.

In a preferred embodiment, the wash solution for a second wash during the first SPE step of the present invention is between 5 and 15% (v/v) acetonitrile in water. In a more preferred embodiment, the wash solution is about 10% (v/v) acetonitrile in water.

In a preferred embodiment, the wash solution for a second wash during the second SPE step of the present invention is between 40% and 70% (v/v) acetonitrile in water. In a more preferred embodiment, the wash solution is about 60% (v/v) acetonitrile in water.

In others preferred embodiments, a third wash is carried out during the first SPE step of the present invention. In a preferred embodiment, the wash solution for a third wash comprises acetonitrile at a concentration between 90% and 100% (v/v). In a more preferred embodiment, the wash solution for a third wash during the first SPE step is acetonitrile at a concentration of about 100% (v/v).

In a preferred embodiment, the first SPE step comprises at least two wash steps, the first one being carried out with a solution comprising between 0.05% and 1% (v/v) TFA in water and the second one being carried out with a solution comprising between 5 and 15% (v/v) acetonitrile in water, and the second SPE step comprises at least three wash steps, the first one being carried out with a solution comprising between 20% and 30% (v/v) formic acid in water, the second one being carried out with a solution comprising between 40% and 70% (v/v) acetonitrile in water, and the third one being carried out with a solution comprising between 90% and 100% (v/v) acetonitrile.

In a more preferred embodiment, the first SPE step comprises at least two wash steps, the first one being carried out with a solution comprising about 0.1% (v/v) TFA in water and the second one being carried out with a solution comprising about 10% (v/v) acetonitrile in water, and the second SPE step comprises at least three wash steps, the first one being carried out with a solution comprising about 25% (v/v) formic acid in water, the second one being carried out with a solution comprising about 60% (v/v) acetonitrile in water, and the third one being carried out with a solution comprising about 100% (v/v) acetonitrile.

In a preferred embodiment, the first SPE step comprises at least two wash steps, the first one being carried out with a solution comprising between 0.05% and 10% (v/v) methanol in water and the second one being carried out with a solution comprising between 5 and 15% (v/v) acetonitrile in water, and the second SPE step comprises at least three wash steps, the first one being carried out with a solution comprising between 0.5% and 50% (v/v) formic acid in water, the second one being carried out with a solution comprising between 30% and 70% (v/v) acetonitrile in water, and the third one being carried out with a solution comprising between 90% and 100% (v/v) acetonitrile.

In a preferred embodiment, the first SPE step comprises at least three wash steps, the first one being carried out with a solution comprising between 5% and 50% (v/v) formic acid in water, the second one being carried out with a solution comprising between 40 and 70% (v/v) acetonitrile in water, and the third one being carried out with a solution comprising between 90% and 100% (v/v) acetonitrile, and the second SPE step comprises at least two wash steps, the first one being carried out with a solution comprising between 0.5% and 15% (v/v) ammonium hydroxide in water, and the second one being carried out with a solution comprising between 30% and 70% (v/v) acetonitrile in water.

In a more preferred embodiment, the first SPE step comprises at least three wash steps, the first one being carried out with a solution comprising about 25% (v/v) FA in water, the second one being carried out with a solution comprising about 60% (v/v) acetonitrile in water, and the third one being carried out with a solution comprising about 100% (v) acetonitrile, and the second SPE step comprises at least two wash steps, the first one being carried out with a solution comprising about 10% (v/v) ammonium hydroxide in water, and the second one being carried out with a solution comprising about 60% (v/v) acetonitrile in water.

In a more preferred embodiment, the first SPE step comprises at least two wash steps, the first one being carried out with a solution comprising between 1% and 20% (v/v) ammonium hydroxide in water and the second one being carried out with a solution comprising between 30 and 70% (v/v) acetonitrile in water, and the second SPE step comprises at least three wash steps, the first one being carried out with a solution comprising between 0.5% and 50% (v/v) formic acid in water, the second one being carried out with a solution comprising between 30% and 70% (v/v) acetonitrile in water, and the third one being carried out with a solution comprising between 90% and 100% (v/v) acetonitrile.

In a more preferred embodiment, the first SPE step comprises at least two wash steps, the first one being carried out with a solution comprising about 10% (v/v) ammonium hydroxide in water and the second one being carried out with a solution comprising about 60% (v/v) acetonitrile in water, and the second SPE step comprises at least three wash steps, the first one being carried out with a solution comprising about 25% (v/v) formic acid in water, the second one being carried out with a solution comprising about 60% (v/v) acetonitrile in water, and the third one being carried out with a solution comprising about 100% (v/v) acetonitrile.

After the at least one wash step carried out during any of the SPE step, elution of the analytes retained in the stationary phase is required. Suitable elution solutions are well known by the skilled person.

In some embodiments, the analytes retained in the stationary phase during the first SPE step are eluted with an elution solution comprising a surfactant and a water miscible polar organic solvent. In other embodiments, the analytes retained in the stationary phase during the first SPE step are eluted with an elution solution comprising a base and a water miscible polar organic solvent. In other embodiments, the analytes retained in the stationary phase during the first SPE step are eluted with an elution solution comprising an acid and a water miscible polar organic solvent.

For example, the water miscible organic solvent may be a polar aprotic, or a protic organic solvent. Non-limiting examples of classes of water miscible organic solvents include, without limitation, esters, nitriles, carboxylic acids, amides, aldehydes, ketones and combinations thereof. It will be understood by those of skill in the art that not every member of the above indicated classes is water miscible, however, those of skill in the art can readily determine the members of a particular class that are water miscible. In yet more preferred embodiments, the water miscible organic solvent is acetonitrile, dimethylformamide, or combinations thereof. In a particularly preferred embodiment, the water miscible organic solvent of the elution solution after the first SPE step of the method of the present invention is acetonitrile. The surfactant of the elution solution can be of any type known by the skilled person, preferably of the nonionic type. In some embodiments, the surfactant is of the nonionic type. In some preferred embodiments, the nonionic surfactant is of the ethoxylate type. In yet more preferred embodiments, the nonionic surfactant of the ethoxylate type is Triton X-100. The base may be selected from the group consisting of water soluble hydroxides, carbonates, oxides and combinations thereof. For example, the base may be a water soluble hydroxide. Suitable hydroxides include inorganic hydroxides, organic hydroxides and combinations thereof. In a preferred embodiment, the base is ammonium hydroxide. The acid of the elution solution can be an organic acid, preferably acetic acid, formic acid or trifluoroacetic acid (TFA).

In a preferred embodiment, the elution solution used after the first SPE step of the method of the present invention comprises Triton X-100 at a concentration between 1% and 5% (v/v), and acetonitrile at a concentration between 20% and 40% (v/v). In a more preferred embodiment, the elution solution consists of about 2% (v/v) Triton X-100 and about 30% (v/v) acetonitrile in water.

In another preferred embodiment, the elution solution used after the first SPE step of the method of the present invention comprises ammonium hydroxide at a concentration between 5% and 15% (v/v), and acetonitrile at a concentration between 50% and 90% (v/v). In a more preferred embodiment, the elution solution consists of about 10% (v/v) ammonium hydroxide and about 75% (v/v) acetonitrile in water.

In another preferred embodiment, the elution solution used after the first SPE step of the method of the present invention comprises trifluoroacetic acid at a concentration between 1% and 15% (v/v), and acetonitrile at a concentration between 50% and 90% (v/v). In a more preferred embodiment, the elution solution consists of about 5% (v/v) trifluoroacetic acid and about 70% (v/v) acetonitrile in water.

In some embodiments, the analytes retained in the stationary phase during the second SPE step are eluted with an elution solution comprising a base and a water miscible polar organic solvent. In other embodiments, the analytes retained in the stationary phase during the second SPE step are eluted with an elution solution comprising an acid and a water miscible polar organic solvent.

The base may be selected from the group consisting of water soluble hydroxides, carbonates, oxides and combinations thereof. For example, the base may be a water soluble hydroxide. Suitable hydroxides include inorganic hydroxides, organic hydroxides and combinations thereof. In a preferred embodiment, the base is ammonium hydroxide. The water miscible organic solvent may be a polar aprotic, or a protic organic solvent. Non-limiting examples of classes of water miscible organic solvents include, without limitation, esters, nitriles, carboxylic acids, amides, aldehydes, ketones and combinations thereof. It will be understood by those of skill in the art that not every member of the above indicated classes is water miscible, however, those of skill in the art can readily determine the members of a particular class that are water miscible. In yet more preferred embodiments, the water miscible organic solvent is acetonitrile, dimethylformamide, or combinations thereof. In a particularly preferred embodiment, the water miscible organic solvent of the elution solution after the second SPE step of the method of the present invention is acetonitrile. The acid of the elution solution can be an organic acid, preferably acetic acid, formic acid or trifluoroacetic acid (TFA).

In a preferred embodiment, the elution solution used after the second SPE step of the method of the present invention comprises ammonium hydroxide at a concentration between 5% and 15% (v/v) and acetonitrile at a concentration between 50% and 90% (v/v). In a more preferred embodiment, the elution solution consists of about 10% (v/v) ammonium hydroxide and about 75% (v/v) acetonitrile in water.

In another preferred embodiment, the elution solution used after the first SPE step of the method of the present invention comprises trifluoroacetic acid at a concentration between 1%) and 15%) (v/v), and acetonitrile at a concentration between 50%) and 90% (v/v). In a more preferred embodiment, the elution solution consists of about 5% (v/v) trifluoroacetic acid and about 70% (v/v) acetonitrile in water.

After elution of the analytes of interest during the first SPE step of the present invention, the pH of the obtained eluates can be modified in order to prepare them for the following steps. In a preferred embodiment, the eluates obtained after the elution during the first SPE are contacted with formic acid, preferably at a concentration between 30% and 70% (v/v) formic acid in water, more preferably at a concentration of about 50% (v/v) formic acid in water, in order to reduce the pH of the solution containing the analytes of interest.

The eluate comprising the purified intact amyloid beta peptides obtained after the second SPE step may then be dried and resuspended in a solution suitable for downstream analysis, such as mass spectrometry. Suitable drying methods are known in the art and may include, but are not limited to, evaporation in a centrifugal vacuum concentrator (e.g. Thermo SpeedVac, Genevac) and lyophilization. In a preferred embodiment, the eluates obtained after the second SPE step of the method for preparing a sample comprising amyloid beta peptides of the present invention are dried in a vacuum concentrator for at least 30 minutes and at a temperature between 30° C. and 50° C. In a more preferred embodiment, the eluates are dried in a vacuum concentrator for around 35 minutes and at a temperature between 40° C. and 47° C.

After drying the eluates, it is necessary to resuspend the analytes in a solution suitable for the specific downstream analysis. In some embodiments, the downstream analysis may be an antibody-based detection method such as ELISA, but in more preferred embodiments, the downstream analysis is mass spectrometry, including liquid chromatography coupled to mass spectrometry. Suitable solutions for the different downstream analysis are known in the art.

In some embodiments of the present invention, the analytes are further subjected to mass spectrometry, including liquid chromatography coupled to mass spectrometry, and the solution in which the dried analytes are resuspended comprises at least two of a surfactant, a reducing agent, a water miscible polar organic solvent and an acid. In other embodiments, said solution in which the dried analytes are resuspended comprises a surfactant and a reducing agent. In other embodiments, said solution in which the dried analytes are resuspended comprises a surfactant, a reducing agent, a polar organic solvent and an acid.

According to the present invention, the surfactant of the solution in which the dried analytes are resuspended can be of any type known by the skilled person, preferably of the nonionic type. In some embodiments, the surfactant is of the nonionic type. In some preferred embodiments, the nonionic surfactant is of the ethoxylate type. In yet more preferred embodiments, the nonionic surfactant of the ethoxylate type is Triton X-100.

According to the present invention, the reducing agent of the solution in which the dried analytes are resuspended can be of any type known by the skilled person, preferably a reducing agent suitable for reducing disulphide bonds. Non-limiting examples of reducing agents suitable for reducing disulphide bonds include organophosphine reducing agents or other reducing agents such as dithiothreitol or β-mercaptoethanol. In preferred embodiments, the reducing agent suitable for reducing disulphide bonds is an organophosphine reducing agent. In more preferred embodiments, the organophosphine reducing agent is tris-carboxyethylphosphine.

According to the present invention, the water miscible polar organic solvent of the solution in which the dried analytes are resuspended can be of any type known by the skilled person, preferably acetonitrile or dimethylformamide. In other embodiments, the polar organic solvent can be a mixture of acetonitrile and dimethylformamide. The water miscible organic solvent may be a polar aprotic, or a protic organic solvent. Non-limiting examples of classes of water miscible organic solvents include, without limitation, ethers, esters, nitriles, carboxylic acids, amides, aldehydes, ketones and combinations thereof. It will be understood by those of skill in the art that not every member of the above indicated classes is water miscible, however, those of skill in the art can readily determine the members of a particular class that are water miscible. In yet more preferred embodiments, the water miscible organic solvent is acetonitrile, dimethylformamide, or combinations thereof.

According to the present invention, the acid of the solution in which the dried analytes are resuspended can be of any type known by the skilled person, preferably an organic acid. In yet more preferred embodiments, the organic acid is a carboxylic acid. In yet more preferred embodiments, the carboxylic acid is a mono-, di-, or tricarboxylic acid. The mono-, di- or tricarboxylic acid may have a pKa of about 4, for example about 3, such as about 2, suitably 1. The mono-, di- or tricarboxylic acid may have a pKa of about 0.5. In a preferred embodiment, the carboxylic acid is a C1-010 haloalkyl mono-, di- or tricarboxylic acid. For example, the carboxylic acid may be a C1-0105 haloalkyl monocarboxylic acid. In yet more preferred embodiments, the carboxylic acid is trifluoroacetic acid (TFA). Thus, in some preferred embodiments, the acid of the solution in which the dried analytes are resuspended is TFA.

All pKa values disclosed herein are as measured in water at 25° C., and 1 atm pressure.

In more preferred embodiments the surfactant is Triton X-100, the reducing agent is tris-carboxyethylphosphine, the polar organic solvent are acetonitrile and dimethylformamide and the acid is TFA.

In some preferred embodiments, the concentration of acetonitrile in the solution in which the dried analytes are dissolved is between 2% and 8% (v/v), more preferably between 3% and 7% (v/v), more preferably between 4% and 6% (v/v) and even more preferably about 5% (v/v).

In some preferred embodiments, the concentration of dimethylformamide in the solution in which the dried analytes are dissolved is between 0.1% and 3% (v/v), more preferably between 0.5% and 2% (v/v), more preferably between 0.5% and 1.5% (v/v) and even more preferably about 1% (v/v).

In some preferred embodiments, the concentration of trifluoroacetic acid (TFA) in the solution in which the dried analytes are dissolved is between 0.1% and 5% (v/v), more preferably between 0.2% and 4% (v/v), more preferably between 0.2% and 3% (v/v), more preferably between 0.2% and 2.5% (v/v) and even more preferably about 0.5% (v/v).

In some preferred embodiments, the concentration of Triton X-100 in the solution in which the dried analytes are dissolved is between 0.01% and 2% (v/v), more preferably between 0.05% and 1% (v/v), more preferably between 0.05% and 0.8% (v/v), more preferably between 0.05% and 0.1% (v/v) and even more preferably about 0.05% (v/v).

In some preferred embodiments, the concentration of tris-carboxyethylphosphine in the solution in which the dried analytes are dissolved is between 0.05% and 0.3% (w/v), more preferably between 0.1% and 0.2% (w/v), more preferably between 0.12% and 0.16% (w/v) and even more preferably about 0.14% (w/v).

In some preferred embodiments, the solution in which the analytes are dissolved is an aqueous solution comprising a surfactant and a reducing agent. In yet more preferred embodiments, the solution in which the dried analytes are dissolved comprises Triton X-100 at a concentration between 0.05% and 0.8% (v/v) and tris-carboxyethylphosphine at a concentration between 0.1% and 0.2% (w/v).

In another preferred embodiment, the solution in which the dried analytes are dissolved comprises Triton X-100 at a concentration between 0.01% and 0.1% (v/v), tris-carboxyethylphosphine at a concentration between 0.1% and 0.2% (w/v) and acetonitrile at a concentration between 3% and 7% (v/v).

In some preferred embodiments, the solution in which the analytes are dissolved is an aqueous solution comprising a surfactant, a reducing agent, a polar organic solvent and an acid. In yet more preferred embodiments, the solution in which the dried analytes are dissolved comprises Triton X-100 at a concentration between 0.01% and 0.1% (v/v), tris-carboxyethylphosphine at a concentration between 0.1% and 0.2% (w/v), acetonitrile at a concentration between 3% and 7% (v/v) and trifluoroacetic acid (TFA) at a concentration between 0.1% and 3% (v/v). In yet more preferred embodiments, the solution in which the dried analytes are dissolved comprises Triton X-100 at a concentration between 0.01% and 0.1% (v/v), tris-carboxyethylphosphine at a concentration between 0.1% and 0.2% (w/v), acetonitrile at a concentration between 3% and 7% (v/v), dimethylformamide at a concentration between 0.1% and 3% (v/v) and trifluoroacetic acid (TFA) at a concentration between 0.1% and 3% (v/v).

In some embodiments, the sample prepared by the method of the present invention is further analysed by liquid chromatography and/or mass spectrometry.

The present invention also refers to a method for preparing a plasma sample comprising amyloid beta peptides for analysis by mass spectrometry, characterized in that it does not comprise immunoprecipitation or digestion of the plasma sample prior the mass spectrometry analysis.

The present invention also refers to a method for preparing a plasma sample comprising amyloid beta peptides for analysis by mass spectrometry, characterized in that it consists essentially of the following steps:

a) Contacting said plasma sample with a denaturing agent,
  b) Performing a first solid phase extraction step on the solution obtained in step a) to recover a first eluate,
  c) Performing a second solid phase extraction step on said first eluate obtained in step b) to recover a second eluate, and
  d) Drying said second eluate obtained in step c) and processing it for analysis by mass spectrometry, wherein the sample obtained from step d) comprises intact amyloid beta peptides Aβ40 and Aβ42.

In a second aspect, the present invention relates to a method for quantification of intact amyloid beta peptides Aβ40 and Aβ42 in a plasma sample by mass spectrometry. In some embodiments, the method for quantification of intact amyloid beta peptides Aβ40 and Aβ42 in a plasma sample by mass spectrometry of the present invention comprises the steps a) to d) of the method for preparing a sample as described herein and further comprises the steps of:

i) Performing a liquid-chromatography step on the solution obtained in step d), to separate the analytes of interest,
  ii) Subjecting the analytes separated in step i) to ionization to generate one or more charged species;
  iii) Separating said one or more charged species according to their ion mobility,
  iv) Detecting said one or more charged species separated in step iii) and measuring their abundances by mass spectrometry; and
  v) Determining the amount or concentration of intact amyloid beta peptides Aβ40 and/or Aβ42 in the plasma sample by comparison of the abundances of the one or more charged species measured in step iv) with a standard curve.

In some embodiments of the present invention, the method for quantification of intact amyloid peptides Aβ40 and Aβ42 in a plasma sample by mass spectrometry comprises performing a chromatography step i) on the solution obtained from a method for preparing a sample comprising amyloid beta peptides as described herein. In preferred embodiments, said chromatography step is a liquid chromatography (LC). In more preferred embodiments, said liquid chromatography is HPLC. In yet more preferred embodiments said chromatography step is micro-liquid chromatography (micro-HPLC).

In some embodiments of the present invention, the method for quantification of intact amyloid beta peptides Aβ40 and Aβ42 in a plasma sample by mass spectrometry comprises a second step ii) wherein the analytes separated in step i) are subjected to ionization to generate one or more charged species.

In some embodiments of the present invention, the ionization the analytes are subjected to is electrospray ionization (ESI) in positive ion mode. The conditions for carrying out the electrospray ionization of the present invention are well-known by the skilled person.

In some embodiments of the present invention, the method for quantification of intact amyloid beta peptides Aβ40 and Aβ42 in a plasma sample by mass spectrometry comprises a third step iii) wherein the one or more charged species obtained in step ii) are separated according to their ion mobility. In preferred embodiments, said one or more charged species are separated by ion-mobility spectrometry (IMS). In a more preferred embodiment, the ion-mobility spectrometry technique used in the methods of the present invention is differential mobility spectrometry (DMS).

In some embodiments of the present invention, after separation of the charged species according to their ion mobility, they are detected and their abundances are measured by mass spectrometry (step iv)). As previously explained, the term "mass spectrometry" encompasses several analytical techniques to determine the mass-to-charge ratio of an analyte or group of analytes. Non-limiting examples of mass-spectrometry techniques includes Ion Trap (3D or Linear), single or triple quadrupole, time of flight, Orbitrap, Fourier-transform ion cyclotron resonance mass spectrometry and their combinations (hybrid instruments).

In a preferred embodiment, the technique for measuring the intensities and abundances of the charged species by mass spectrometry is multiple reaction monitoring (MRM) in a triple quadrupole instrument.

In some embodiments of the present invention, the method for quantification of intact amyloid beta peptides $A\beta40$ and $A\beta42$ in a plasma sample by mass spectrometry comprises a fifth step v) wherein the amount or concentration of said peptides is determined by comparison of the abundances of the analytes measured in iv) with a standard curve.

Therefore, a calibration curve is preferably prepared using increasing concentration of at least one standard in order to quantify the amount or concentration of an analyte in a sample analysed by mass spectrometry. In the context of the present invention, as $A\beta40$ and $A\beta42$ are the peptides to be preferably quantified, labelled $^{15}N$-$A\beta40$ and 15N-$A\beta42$ are preferably used as standards for the calibration curve.

The calibration curve can be prepared with buffer solutions, such as PBS, comprising BSA, as previously described in the prior art. However, in preferred embodiments of the present invention, calibration curves are prepared with plasma, which provides for several advantages, such as providing equal recoveries for both standards and analytes, and equalising matrix effects that can otherwise adversely affect quantitation. In more preferred embodiments, calibration curves are prepared with human plasma.

In addition, internal standards are used as controls for the quality of the different steps of the methods of the present invention as well as for signal normalization. Therefore, internal standards may be added to the solutions for preparing the calibration curves and to the samples to be analysed by mass spectrometry, in order to assure quality of the different steps.

In some embodiments, the solutions for the calibration curves and the samples are spiked with labelled $^{2}H$-$A\beta40$ and $^{2}H$-$A\beta42$ as internal standards. In other embodiments, the solutions for the calibration curves and the samples are spiked with labelled $^{13}C$-$A\beta40$ and $^{13}C$-$A\beta42$ as internal standards. In other embodiments, the solutions for the calibration curves and the samples are spiked with $^{2}H$-$A\beta40$ and $^{13}C$-$A\beta42$ or $^{2}H$-$A\beta42$ and $^{13}C$-$A\beta40$ as internal standards.

In other embodiments, the present invention relates to a method for quantification of intact amyloid beta peptides $A\beta40$ and $A\beta42$ in a plasma sample by mass spectrometry characterized in that it does not comprises a step in which the concentration of said peptides is determined by comparison of the abundances of the analytes measured in iv) with a standard curve. In such embodiments, the method for quantification is a semi-quantitative method in which the use of internal standards aims to quantify the abundances of said analytes without comparison with a standard curve.

The samples comprising amyloid beta peptides used in the methods of the present invention are preferably plasma samples. The volume of the plasma sample used in step a) of the method for preparation of a sample for analysis by mass spectrometry can be determined by the skilled person taking into account the specific protocol of mass spectrometry to be followed.

However, one of the advantages of the methods of the present invention is that it is possible to reduce the volume of the sample required for obtaining accurate values of the concentration of amyloid beta peptides $A\beta40$ and $A\beta42$ to identify early stages of neurodegenerative diseases, such as Alzheimer's disease, in a subject. Reduction of the volume of the plasma sample required in the methods of the present invention is especially convenient for large screening studies.

Thus, the volume of sample used in step a) of the methods for preparing a plasma sample comprising amyloid beta peptides for analysis by mass spectrometry is between 100 μL and 400 μL. In a preferred embodiment, the volume of sample is between 150 μL and 300 μL. In a more preferred embodiment, the volume of sample is between 200 μL and 250 μL. In a yet more preferred embodiment, the volume of sample is about 200 μL.

In a third aspect, the present invention refers to an aqueous solution for processing a dried eluate to be analysed by mass spectrometry comprising at least two of a surfactant, a reducing agent, a water miscible polar organic solvent and an acid. In other embodiments, said aqueous solution comprises a surfactant and a reducing agent. In other embodiments, said solution comprises a surfactant, a reducing agent, a polar organic solvent and an acid.

According to the present invention, the surfactant of the solution in which the dried analytes are processed can be of any type known by the skilled person, preferably of the nonionic type. In some embodiments, the surfactant is of the nonionic type. In some preferred embodiments, the nonionic surfactant is of the ethoxylate type. In yet more preferred embodiments, the nonionic surfactant of the ethoxylate type is Triton X-100.

According to the present invention, the reducing agent of the solution in which the dried analytes are processed can be of any type known by the skilled person, preferably a reducing agent suitable for reducing disulphide bonds. Non-limiting examples of reducing agents suitable for reducing disulphide bonds include organophosphine reducing agents or other reducing agents such as dithiothreitol or β-mercaptoethanol. In preferred embodiments, the reducing agent suitable for reducing disulphide bonds is an organophosphine reducing agent. In more preferred embodiments, the organophosphine reducing agent is tris-carboxyethylphosphine.

According to the present invention, the water miscible polar organic solvent of the solution in which the dried analytes are processed can be of any type known by the skilled person. The water miscible organic solvent may be a polar aprotic, or a protic organic solvent. Non-limiting examples of classes of water miscible organic solvents include, without limitation, esters, nitriles, carboxylic acids, amides, aldehydes, ketones and combinations thereof. It will be understood by those of skill in the art that not every member of the above indicated classes is water miscible, however, those of skill in the art can readily determine the members of a particular class that are water miscible. In yet more preferred embodiments, the water miscible organic solvent is acetonitrile, dimethylformamide, or combinations thereof.

According to the present invention, the acid of the solution in which the dried analytes are processed can be of any type known by the skilled person, preferably an organic acid. In yet more preferred embodiments, the organic acid is a carboxylic acid. In yet more preferred embodiments, the carboxylic acid is a mono-, di-, or tricarboxylic acid. The mono-, di- or tricarboxylic acid may have a pKa of about 4, for example about 3, such as about 2, suitably 1. The mono-, di- or tricarboxylic acid may have a pKa of about 0.5. In a preferred embodiment, the carboxylic acid is a C1-C10 haloalkyl mono-, di- or tricarboxylic acid. For example, the carboxylic acid may be a C1-C5 haloalkyl monocarboxylic acid. In yet more preferred embodiments, the carboxylic acid is trifluoroacetic acid (TFA). Thus, in some preferred embodiments, the acid of the solution in which the dried analytes are processed is TFA.

In more preferred embodiments the surfactant is Triton X-100, the reducing agent is tris-carboxyethylphosphine, the polar organic solvents are acetonitrile and dimethylformamide and the acid is TFA.

In more preferred embodiments, the aqueous solution for resuspending a dried eluate to be analysed by mass spectrometry of the present invention comprises Triton X-100 at a concentration between 0.01% and 0.1% (v/v) and tris-carboxyethylphosphine at a concentration between 0.1% and 0.2% (w/v).

In other more preferred embodiments, the aqueous solution for processing a dried eluate to be analysed by mass spectrometry of the present invention comprises Triton X-100 at a concentration between 0.010% and 1% (v/v), tris-carboxyethylphosphine at a concentration between 0.1% and 0.2% (w/v), acetonitrile at a concentration between 3% and 7% (v/v), dimethylformamide at a concentration between 0.1% and 3% (v/v) and trifluoroacetic acid (TFA) at a concentration between 0.1% and 3% (v/v). The invention will be more fully understood by reference to the following examples. They should not, however, be construed as limiting the scope of this invention.

EXAMPLES

Example 1: Preparation of Plasma Samples for Analysis by Mass Spectrometry

Calibration Curves and Quality Control

Calibration curves and quality control samples were prepared using human plasma and $^{15}$N-Aβ40 and $^{15}$N-Aβ42 labelled standards (rPeptide, Watkinsville, GA, USA). Calibration ranges from 50 to 3000 pg/ml and 10 to 100 pg/ml were used for preparing series of standards of $^{15}$N-Aβ40 and $^{15}$N-Aβ42, respectively.

The series of standards for the calibration curve, the quality control samples and the plasma samples from human subjects to be further analysed were all spiked with $^{2}$H-Aβ40 and $^{2}$H-Aβ42 custom-made labelled as internal standards for quality control and signal normalization (Bachem, Bubendorf, Switzerland).

Preparation of Plasma Samples for Analysis by Mass Spectrometry

Plasma samples obtained from human subjects were prepared following different protocols (A, B, C or D) depending on the combination of SPE cartridges to be subsequently used.

Protocol A: The samples were first spiked with the internal standards of choice. Then, the samples were denaturised by contacting 400 μl of 50% formic acid (FA) in water with 200 μl of human plasma. After denaturation, the amyloid peptides were purified using two consecutive SPE steps.

The first SPE consisted in a reversed phase SPE, for which HLB Prime extraction plates (OASIS HLB Prime 96 well plates, 30 mg, Waters, Milford, MA, USA, part number 186008054) were used. Suitable conditions for the first SPE are outlined below:

Solvation: 1 ml of acetonitrile
Conditioning: 1 ml of 0.1% FA (formic acid) in water
Sample loading
Wash 1:0.5 ml of 5% Methanol
Wash 2: 0.5 ml 10% acetonitrile in water
Elution: 0.4 ml 0.1% TFA in acetonitrile/water 70/30

Acidification of the eluates by adding 10 μl of 50% FA in water

After the first SPE, the eluates were subjected to a second SPE, in this case, a Mixed-Mode Reversed Phase-Cation Exchange SPE using the MCX extraction plate (OASIS MCX 96 well μElution Plates, 30 μm, 2 mg, Waters, Milford, MA, USA, part number 186001830BA). Suitable conditions for the second SPE are outlined below:

Solvation: 0.2 ml of methanol
Conditioning: 0.2 ml of 5% FA in water
Sample loading: acidified eluates from SPE 1
Wash 1: 0.4 ml of 5% FA in water
Wash 2: 0.4 ml of 40% acetonitrile in water
Wash 3: 0.4 ml of acetonitrile 100%
Elution: 100 μl of acetonitrile/water/ammonium hydroxide 75/15/10

After the second SPE, the eluates were evaporated to dryness for 35 minutes at 45° C. in a vacuum concentrator. Then, the dried samples were resuspended with 25 μl of AB solvent, an in-house optimized solution which was composed of:

Acetonitrile 100%: 2.5 ml
Dimethylformamide (DMF) 100%: 0.5 ml
TFA 25% in water: 1 ml
Triton X-100 10% in water: 0.25 ml
Tris-carboxyethylphosphine: 70 mg
Water: take to volume 50 ml, in a volumetric flask Protocol B: The samples were first spiked with the internal standards of choice. Then, the samples were denaturised by contacting 400 μl of 50% formic acid (FA) in water with 200 μl of human plasma. After denaturation, the amyloid peptides were purified using two consecutive SPE steps.

The first SPE consisted in a reversed phase SPE, for which HLB extraction plates (OASIS HLB, 96 well plates, 30 μm, 30 mg, Waters, Milford, MA, USA, part number WAT058951) were used. Suitable conditions for the first SPE are outlined below:

Solvation: 1 ml of acetonitrile
Conditioning: 1 ml of 0.1% TFA (trifluoroacetic acid) in water
Sample loading
Wash 1: 1 ml of 0.1% TFA
Wash 2: 0.5 ml 10% acetonitrile in water
Elution: 0.7 ml of 2% Triton X-100 in acetonitrile/water 30/70
Acidification of the eluates by adding 10 μl of 50% FA in water After the first SPE, the eluates were subjected to a second SPE, in this case, a Mixed-Mode Reversed Phase-Cation Exchange SPE using the MCX extraction plate (OASIS MCX 96 well μElution Plates, 30 μm, 2 mg, Waters, Milford, MA, USA, part number 186001830BA). Suitable conditions for the second SPE are outlined below:

Solvation: 0.2 ml of methanol
Conditioning: 0.2 ml of 25% FA in water
Sample loading: acidified eluates from SPE 1
Wash 1: 0.4 ml of 25% FA in water
Wash 2: 0.4 ml of 60% acetonitrile in water
Wash 3: 0.4 ml of acetonitrile 100%
Elution: 100 μl of acetonitrile/water/ammonium hydroxide 75/15/10

After the second SPE, the eluates were evaporated to dryness for 35 minutes at 45° C. in a vacuum concentrator. Then, the dried samples were resuspended with 25 μl of AB solvent, an in-house optimized solution which was composed 5% v/v AcN, 1% v/v dimethylformamide, 0.5% v/v TFA, 0.05% v/v Triton X-100, 0.14% w/v tris-carboxyethylphosphine in water.

Protocol C: The samples were first spiked with the internal standards of choice. Then, the samples were denaturised by contacting 400 µl of 50% formic acid (FA) in water with 200 µl of human plasma. After denaturation, the amyloid peptides were purified using two consecutive SPE steps.

The first SPE consisted in a Mixed-Mode Reversed Phase-Cation Exchange SPE using the MCX extraction plate (OASIS MCX 96 well Plates, 30 µm, 30 mg, Waters, Milford, MA, USA, part number 186000248). were used. Suitable conditions for the first SPE are outlined below:
  Solvation: 1 ml of methanol
  Conditioning: 1 ml of 25% FA in water
  Sample loading
  Wash 1: 1 ml of 25% FA in water
  Wash 2: 1 ml of 60% acetonitrile in water (60/40)
  Wash 3: 1 ml of acetonitrile 100%
  Elution: 2×400 µl of acetonitrile/water/ammonium hydroxide (75/15/10)

After the first SPE, the eluates were subjected to a second SPE, in this case, a Mixed-Mode Reversed Phase-Anion Exchange SPE using the MAX µElution Plates (OASIS MAX µElution plates, Waters, Milford, MA, USA, part number 186001829. Suitable conditions for the second SPE are outlined below:
  Solvation: 0.3 ml of Methanol
  Conditioning: 0.4 ml NH4OH 10%
  Sample loading
  Wash 1: 0.4 ml NH4OH 10%
  Wash 2: 0.4 ml of Acetonitrile/Water (60/40)
  Elution: 2×50 µl of Acetonitrile/Water 70/30, 5% TFA After the second SPE, the eluates were evaporated to dryness for 35 minutes at 45° C. in a vacuum concentrator. Then, the dried samples were resuspended with 25 µl of AB solvent, an in-house optimized solution which was composed 5% v/v AcN, 1% v/v dimethylformamide, 0.5% v/v TFA, 0.05% v/v Triton X-100, 0.14% w/v tris-carboxyethylphosphine in water.

Protocol D: The samples were first spiked with the internal standards of choice. Then, the samples were denaturised by contacting 400 µl of 25% NH4OH in water with 200 µl of human plasma. After denaturation, the amyloid peptides were purified using two consecutive SPE steps.

The first SPE consisted in a Mixed-Mode Reversed Phase-Anion Exchange SPE, for which OASIS MAX 96 Well Plates (30 µm, 30 mg, Waters, Milford, MA, USA, part number 186000373) were used. Suitable conditions for the first SPE are outlined below:
  Solvation: 1 ml of Methanol
  Conditioning: 1 ml NH4OH 10%
  Sample load
  Wash 1: 1 ml of NH4OH 10%
  Wash 2: 1 ml of Acetonitrile/Water 60/40
  Elution: 2×400 µl of Acetonitrile/Water 70/30, 5% Trifluoroacetic acid After the first SPE, the eluates were subjected to a second SPE, in this case, a Mixed-Mode Reversed Phase-Cation Exchange SPE using the MCX extraction plate (OASIS MCX 96 well µElution Plates, 30 µm, 2 mg, Waters, Milford, MA, USA, part number 186001830BA). Suitable conditions for the second SPE are outlined below:
  Solvation: 0.2 ml of methanol
  Conditioning: 0.2 ml of 25% FA in water
  Sample load
  Wash 1:0.4 ml of 25% FA in water Wash 2: 0.4 ml of 60% acetonitrile in water
  Wash 3: 0.4 ml of acetonitrile 100%
  Elution: 100 µl of acetonitrile/water/ammonium hydroxide 75/15/10

After the second SPE, the eluates were evaporated to dryness for 35 minutes at 45° C. in a vacuum concentrator. Then, the dried samples were resuspended with 25 µl of AB solvent, an in-house optimized solution which was composed of:
  Acetonitrile 100%: 2.5 ml
  Dimethylformamide (DMF) 100%: 0.5 ml
  TFA 25% in water: 1 ml
  Triton X-100 10% in water: 0.25 ml
  Tris-carboxyethylphosphine: 70 mg
  Water: take to volume 50 ml, in a volumetric flask Calibration curves and the quality control samples were also subjected to the same preparation protocol in each case.

Example 2: Analysis of Plasma Samples by Mass Spectrometry

The plasma samples prepared in example 1 were later analysed by mass spectrometry following the methods for quantification of amyloid peptides of the present invention.

The analytical system used for quantification of amyloid peptides was composed of the following modules:
  M3 Micro-HPLC dual pump (trap-elute) chromatograph, fitted with a CTC autosampler and column oven (Sciex, Framingham, MA, USA).
  6500+ QTRAP Hybrid Triple Quadrupole-Linear Ion Trap Mass Spectrometer coupled to a SelexION differential mobility spectrometry—DMS—interface (Sciex, Framingham, MA, USA).

After injection, samples were loaded on the trap column (YMC Triart C18, 12 nm, 3 µm, 5×0.3 mm. YMC, Dinslaken, Germany). A trapping flow rate of 50 µl/min with 0.5% TFA and 5% Dimethylsulfoxide (DMSO) in water was used for two minutes. After that, the trapping valve was switched and analytes were eluted from the trap column to the analytical column and MS system. The following chromatographic conditions were used:
  Phase A: 0.1% FA in water
  Phase B: 0.1% FA in acetonitrile
  Flow Rate: 15 µl/min
  Column: HALO Protein C18, 400 Å, 3.4 µm, 0.3×50 mm (Advanced Materials Technology, Wilmington, DE, USA)
  Column Temperature: 55° C.
  Gradient: 15% B for 0.3 min, linear ramp up to 40% B at min 3.5, rise to 90% B in 0.1 min and for 0.3 min, back to initial conditions (15% B) in 0.1 min and for 3 min to allow column re-equilibration.
  At min 5.5, the analytical valve was switched and a system was washed with 0.1% Triton X-100 in TFE/water 80/20. After that, the trap column was equilibrated with the loading solvent (5% DMSO 0.5% TFA in water).

Sample acquisition started when the trapping valve was switched and analytes were eluted to the analytical column. After chromatographic separation took place, analytes entered the mass spectrometer's ion source and were subject to electrospray ionisation (ESI) in positive ion mode. Once in the gas phase, analytes were subject to differential mobility spectrometry (DMS) to be separated, as much as possible, from interfering matrix ions.

The specific combination of DMS with microLC resulted in reduction of background noise and increased sensitivity.

After DMS separation, ions (charged species of the analytes of interest) were analysed by multiple reaction monitoring (MRM) in a triple quadrupole instrument. Briefly, precursor (pseudomolecular) ions were filtered in the first quadrupole (Q1), fragmented in the second quadrupole (Q2 or collision cell) by collisions with a target gas (a process known as Collision-Induced Dissociation, CID, or Collisionally Activated Dissociation, CAD), and the fragments of interest were filtered in the third quadrupole (Q3) and reached the detector.

Precursor ions with charge state of five (z=5) were selected in Q1, fragmented in Q2 by collisions with nitrogen gas, and fragments were analysed in Q3 (also with z=5). MRM acquisition parameters are summarized below:

| Species | Q1 Mass | Q3 Mass | Time (msec) | Collision Energy | Collision cell exit potential |
|---|---|---|---|---|---|
| $A\beta40$ | 867.0 | 843.6 | 45 | 25 | 18 |
| $A\beta42$ | 903.8 | 886.0 | 45 | 24 | 20 |
| $^{15}N$-$A\beta40$ | 877.5 | 853.9 | 45 | 25 | 18 |
| $^{15}N$-$A\beta42$ | 914.8 | 896.7 | 45 | 24 | 20 |
| $^{2}H$-$A\beta40$ | 872.1 | 848.6 | 45 | 25 | 18 |
| $^{2}H$-$A\beta42$ | 909.4 | 891.5 | 45 | 25 | 20 |

For $A\beta40$, $^{15}N$-$A\beta40$ and $^{2}H$-$A\beta40$, $b_{39}{}^{5+}$ product ions were analysed in Q3. For $A\beta42$, $^{15}N$-$A\beta42$ and $^{2}H$-$A\beta42$, $b_{41}{}^{5+}$ product ions were analysed in Q3. All the molecular masses in the table above are average masses.

The following acquisition parameters were the same for all the species: Source Temperature 250° C., Curtain Gas 30 pounds per square inch (psi), IonSpray Voltage 4800 volts (v), Ion Source Gas 1 (nebulizing) 30 psi, Ion source Gas 2 (desolvating) 50 psi, Declustering Potential 85 v and Entrance Potential 10 v. Both filtering quadrupoles, Q1 and Q3, are operated at Unit Resolution.

A linear equation was fitted to peak area ratios ($^{15}N$-$A\beta40/^{2}H$-$A\beta40$ and $^{15}N$-$A\beta42/^{2}H$-$A\beta42$) versus concentration data by means of linear regression for calibration curve samples. In the case of quality control samples, response ratios ($^{15}N$-$A\beta40/2H$-$A\beta40$ and $^{15}N$-$A\beta42/^{2}H$-$A\beta42$) were interpolated in their corresponding calibration curve and the back-calculated concentrations obtained and evaluated. For the samples of interest, samples response ratios ($A\beta40/^{2}H$-$A\beta40$ and $A\beta42/^{2}H$-$A\beta42$) were interpolated in their corresponding calibration curve and the calculated concentrations obtained. Regression analysis was performed with MultiQuant 3.0.3 software (Sciex, Framingham, MA, USA).

Example 3: Quantification of Intact Amyloid Beta Peptides Aβ40 and Aβ42 in Plasma Samples Prepared and Analysed According to the Present Invention 20 replicates from two different plasma samples (sample A and sample B) were prepared following the method as described in example 1 (protocol B) and example 2, and further analysed by mass spectrometry following the method as explained in example 2.

The values obtained by interpolation in calibration curves of quantification of amyloid beta peptides conducted on the 20 replicates of each plasma sample are shown in Table 1 below.

As it can be seen in Table 1, the coefficient of variation for quantification (% CV) of Aβ40 is below 4%, while the coefficient of variation for quantification of Aβ42 is around 6%. These coefficients of variation represents small variabilities which makes the methods of the present invention suitable for detecting small differences in Aβ peptides between groups.

TABLE 1

Quantification of Aβ40 and Aβ42 in plasma samples

| | Sample A | | Sample B | |
|---|---|---|---|---|
| | Aβ40 | Aβ42 | Aβ40 | Aβ42 |
| | 248.8 | 47.0 | 189.2 | 49.8 |
| | 249.6 | 44.3 | 175.4 | 47.5 |
| | 236.3 | 42.2 | 180.0 | 50.4 |
| | 251.8 | 46.0 | 184.5 | 55.9 |
| | 251.9 | 42.0 | 182.7 | 56.8 |
| | 254.6 | 44.5 | 168.9 | 53.9 |
| | 243.1 | 45.6 | 172.3 | 51.4 |
| | 238.4 | 46.7 | 175.3 | 57.0 |
| | 235.3 | 39.6 | 169.1 | 49.6 |
| | 237.5 | 44.3 | 169.0 | 47.4 |
| | 235.3 | 46.0 | 169.0 | 51.1 |
| | 238.4 | 43.3 | 166.0 | 52.1 |
| | 248.5 | 42.3 | 174.7 | 48.0 |
| | 235.4 | 45.5 | 166.1 | 51.4 |
| | 260.6 | 45.5 | 173.0 | 53.2 |
| | 240.1 | 48.8 | 173.9 | 52.4 |
| | 251.8 | 44.3 | 176.0 | 50.8 |
| | 242.7 | 39.0 | 179.0 | 48.1 |
| | 247.0 | 46.3 | 184.5 | 54.8 |
| | 245.6 | 40.7 | 173.5 | 57.5 |
| Mean | 244.63 | 44.19 | 175.10 | 51.96 |
| SD | 7.46 | 2.57 | 6.51 | 3.21 |
| % CV | 3.05 | 5.81 | 3.72 | 6.17 |

Absolute values of quantification of Aβ40 in human plasma were similar to those obtained by the methods of MS and immunological ligand-binding assay (LBA) methods (mostly ELISA) known in the art. However, for quantification of Aβ42, the levels observed with the methods of the present invention were significantly higher.

In addition, the method of the present invention allowed quantification of intact peptides Aβ40 and Aβ42 while other methods known in the art, such as that of Bateman's group, detect truncated peptides (Ovod et al., Amyloid B concentrations and stable isotope labelling kinetics of human plasma specific to central nervous system amyloidosis, Alzheimer's and Dementia, 2017 October; 13(10): 1185).

Example 4: Detection of Small Changes of Aβ Species in a Sample

In further studies, the ability to detect small amyloid concentration differences in human plasma was investigated. Thus, 200 μl and 220 μl of plasma sample were prepared following the method of example 1, protocol B, and further analysed by mass spectrometry following the method as explained in example 2. In this case, analyte ratios (area $^{14}N$-$A\beta40/^{15}N$-$A\beta40$ and $^{14}N$-$A\beta42/^{15}N$-$A\beta42$) were compared.

In this example, amyloid concentration in plasma samples was exactly the same. However, this is not true for absolute amounts, as there is a 10% difference the volumes employed. This situation mimics a 10% concentration difference in real samples.

Table 2 shows the results for the quantification of Aβ42 and Aβ40 conducted in several replicates of the same plasma sample where the starting volume of sample was either 200 μl and 220 μl following the methods of the present invention as described in examples 1 and 2.

The results demonstrate that the increase in 10% of the volume of plasma sample results in an increase of 10% and 9% of the amount of Aβ42 and Aβ40, respectively, as quantified by the methods of the present invention.

TABLE 2

Determination of a 10% increase of Aβ40 and
Aβ42 peptides in plasma samples

| | Aβ42 | | Aβ40 | |
|---|---|---|---|---|
| | 200 μl | 220 μl | 200 μl | 220 μl |
| | 3.99E– | 4.41E– | 1.62E– | 1.80E– |
| | 3.95E– | 4.40E– | 1.70E– | 1.81E– |
| | 3.58E– | 4.17E– | 1.73E– | 1.85E– |
| | 3.97E– | 4.36E– | 1.70E– | 1.90E– |
| | 4.08E– | 4.26E– | 1.69E– | 1.80E– |
| | 3.98E– | 4.51E– | 1.65E– | 1.85E– |
| | 4.08E– | 3.89E– | 1.70E– | 1.87E– |
| | 4.26E– | 4.32E– | 1.69E– | 1.83E– |
| | 4.01E– | 4.14E– | 1.70E– | 1.84E– |
| | 3.88E– | 4.57E– | 1.63E– | 1.82E– |
| | 3.48E– | 4.30E– | 1.75E– | 1.81E– |
| | 3.77E– | 4.17E– | | |

| | Aβ42 | | | Aβ40 | |
|---|---|---|---|---|---|
| | 200 μl | 220 μl | | | |
| Mean | 0.3919 | 0.4292 | Mean | 0.1687 | 0.1835 |
| SD | 0.0217 | 0.0184 | SD | 0.0040 | 0.0031 |
| % CV | 5.55 | 4.28 | % CV | 2.34 | 1.71 |
| | | 10 | | | 9 |
| p-value | 0.0001642 | | p-value | 5.5035E–09 | |

Example 5: Diagnostic Performance of the Methods
of the Present Invention

Figure 2:
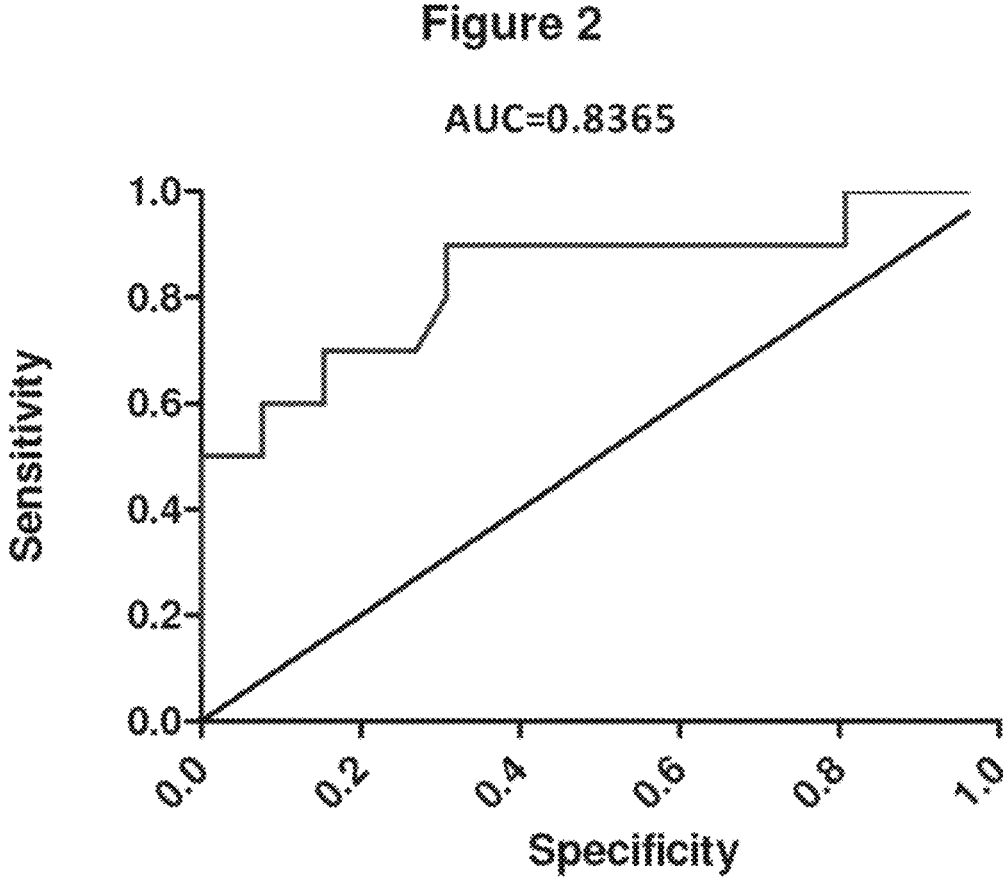
FIG. 2 shows a graph of the ROC curve calculated for the Aβ42/Aβ40 ratios of FIG. 1.

Samples from 36 individuals previously characterized by positron emission tomography (PET) (26 PET negative individuals and 14 PET positive individuals) were prepared following the method as explained in example 1 and further analysed by mass spectrometry following the method as explained in example 2. The Aβ42/Aβ40 ratios were calculated and are shown in FIG. 1. For PET negative individuals, the mean of the values of the Aβ42/Aβ40 ratios was 0.184 with a standard deviation of 0.02, while for PET positive individuals, the mean of the values of the Aβ42/Aβ40 ratios was 0.152 with a standard deviation of 0.03 (p-value<0.001). The ROC curve showed an AUC=0.8365 (FIG. 2).

As explained in the background section, Aβ42/Aβ40 concentration ratio is used as a brain amyloidosis biomarker in the early stages of Alzheimer's disease, wherein lower Aβ42 concentrations are found when amyloid plaques are present. Therefore, these results demonstrated that the methods of the present invention can be used not only to monitor Aβ changes as a response to a therapy, but also with diagnostic purposes since they allow for distinction between PET Positive and PET Negative individuals.

Example 6: Comparison of Different Combinations
of SPE Cartridges

Figure 4:
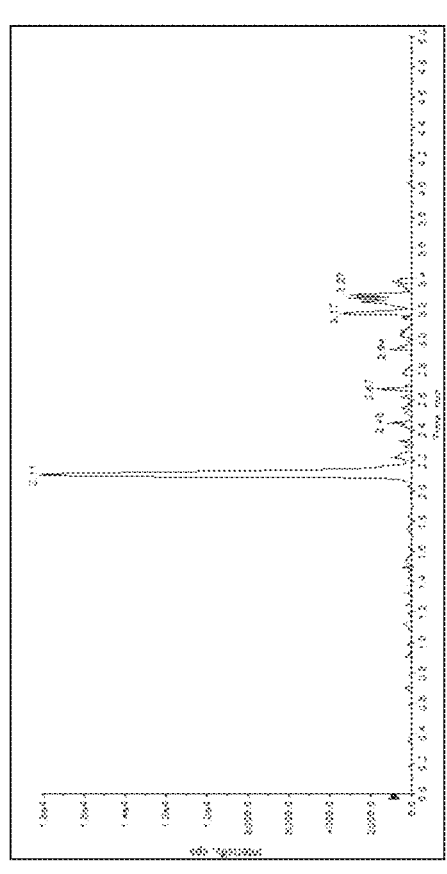
FIG. 4 shows the chromatograms obtained for a plasma sample subjected to a 1$^{st}$ SPE step, a reversed-phase (HLB prime) followed by a second SPE MCX, according to protocol A. The left trace relates to Aβ40, and the right trace to Aβ42.
Figure 4:
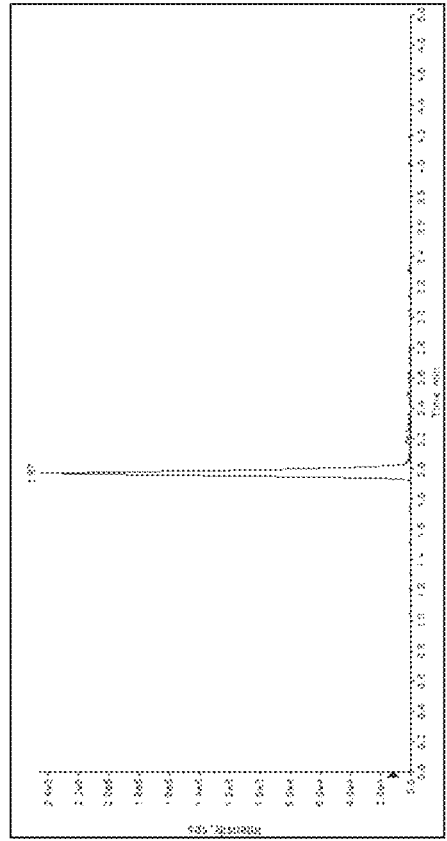

Different tests for SPE cartridge combination were carried out, based on the preparation of the samples for mass spectrometry as explained in example 1 and then analysed as described in Example 2. The respective chromatographic traces extracted for Aβ40 and Aβ42 are shown in FIGS. 4 to

30

Figure 3:
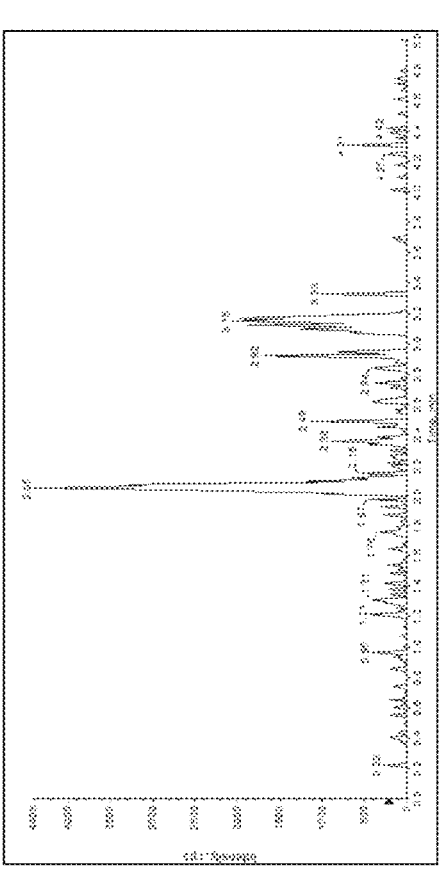
FIG. 3 shows the chromatograms obtained for a plasma sample subjected to a sole SPE step, a Mixed-Mode Reversed Phase-Cation Exchange (MCX). The left trace relates to Aβ40, and the right trace to Aβ42.
Figure 3:
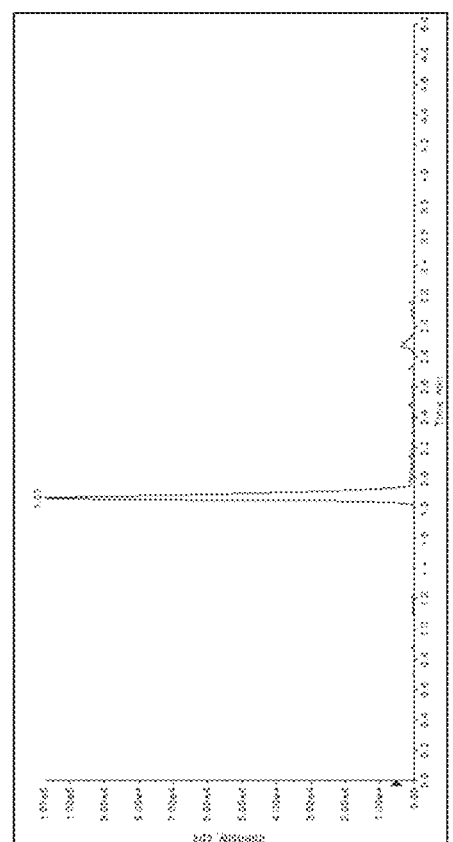

8. For comparison, the use of a single SPE step (a Mixed-Mode Reversed Phase-Cation Exchange) was also evaluated (FIG. 3). The use of single reversed-mode SPE was not evaluated as the resulting eluate is not susceptible of being successfully analysed by Micro-LC because of duration of the chromatographic column.

Figure 5:
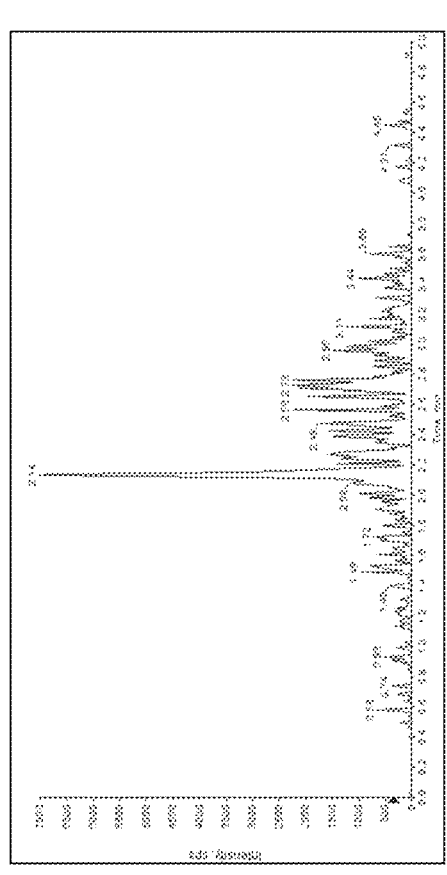
FIG. 5 shows the chromatograms obtained for a plasma sample subjected to a 1$^{st}$ SPE step MCX followed by a second SPE HLB. The left trace relates to Aβ40, and the right trace to Aβ42.
Figure 5:
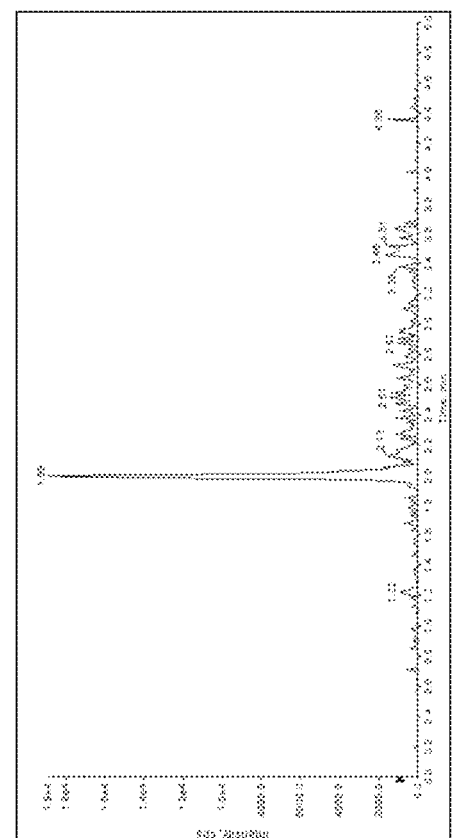
Figure 6:
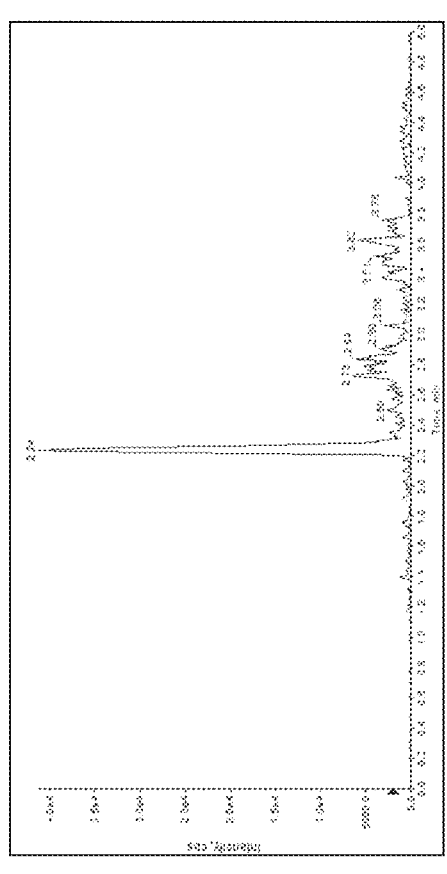
FIG. 6 shows the chromatograms obtained for a plasma sample subjected to a 1$^{st}$ SPE step HLB followed by a second SPE MCX, according to protocol B. The left trace relates to Aβ40, and the right trace to Aβ42.
Figure 6:
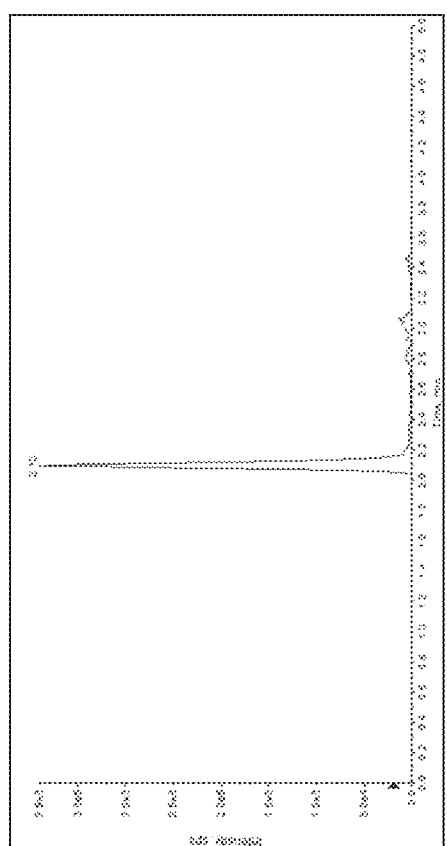

Thus, the following SPE combinations were evaluated:
FIG. 4 shows the chromatographic traces extracted for Aβ40 (left) and Aβ42 (right) when the plasma sample was contacted with an acidic denaturing agent and separated firstly with a reversed-mode SPE (HLB Prime) following by a second Mixed-Mode Reversed Phase-Cation Exchange SPE (MCX) following protocol A.
FIG. 6 shows the chromatographic traces extracted for Aβ40 (left) and Aβ42 (right) when the plasma sample was contacted with an acidic denaturing agent and separated firstly with a reversed-mode SPE (HLB) following by a second Mixed-Mode Reversed Phase-Cation Exchange SPE (MCX) following Protocol B.
FIG. 5 shows the chromatographic traces extracted for Aβ40 (left) and Aβ42 (right) when the plasma sample was contacted with an acidic denaturing agent and separated firstly with a Mixed-Mode Reversed Phase-Cation Exchange SPE (MCX), followed by a second reversed-mode SPE (HLB).

It is clearly shown in the figures that the trace extracted for Aβ40 (left) and Aβ42 (right) when the first SPE is a MCX followed by a HLB are worse than those obtained by using a first HLB or HLB Prime followed by a MCX. In addition, when compared with a single SPE step, as it is already known in the prior art (FIG. 3), the traces are much more intense which demonstrate that the combination of two consecutive SPE steps provides for a better signal to noise ratio and thus, sensitivity.

Figure 8:
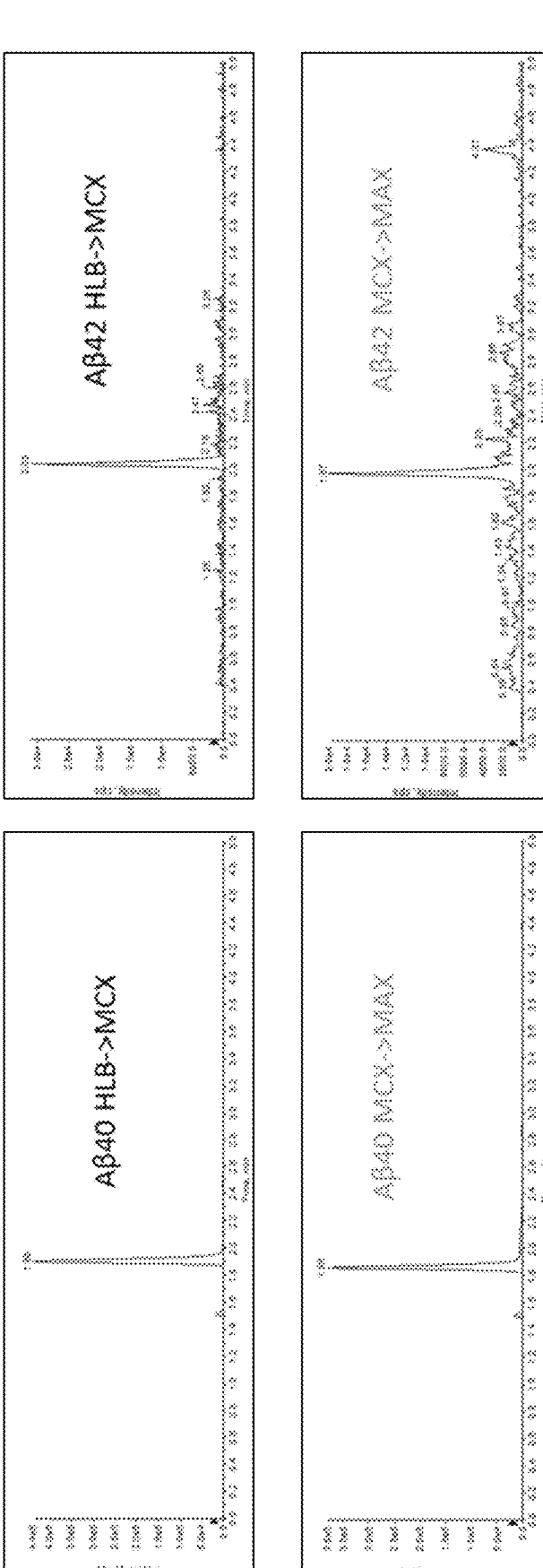
FIG. 8 shows the chromatograms obtained for a plasma sample subjected to a 1$^{st}$ SPE step MCX followed by a second SPE MAX, according to protocol C in comparison with the combination of a first HLB followed by a second MCX. The left trace relates to Aβ40, and the right trace to Aβ42.

FIG. 8 shows the chromatographic traces extracted for Aβ40 (left) and Aβ42 (right) when the plasma sample was contacted with an acidic denaturing agent and separated firstly with a Mixed-Mode Reversed Phase-Cation Exchange SPE (MCX) following by a second Mixed-Mode Reversed Phase-Anion Exchange SPE (MAX) (protocol C). Said traces are compared with the traces obtained when the plasma sample, denaturalized with an acidic agent, was separated firstly with a reversed-mode SPE (HLB) following by a second Mixed-Mode Reversed Phase-Cation Exchange SPE (MCX).

The chromatographic traces shown in FIG. 8 demonstrate that the use of a first MCX SPE followed by a second MAX SPE allows for obtaining discriminative peaks for Aβ40 and Aβ42, in a similar way, though not so intense at this time, than when using a first HLB SPE followed by a MCX SPE. However, when the first SPE is substituted by a HLB, recovery of both analytes is very low.

Figure 7:
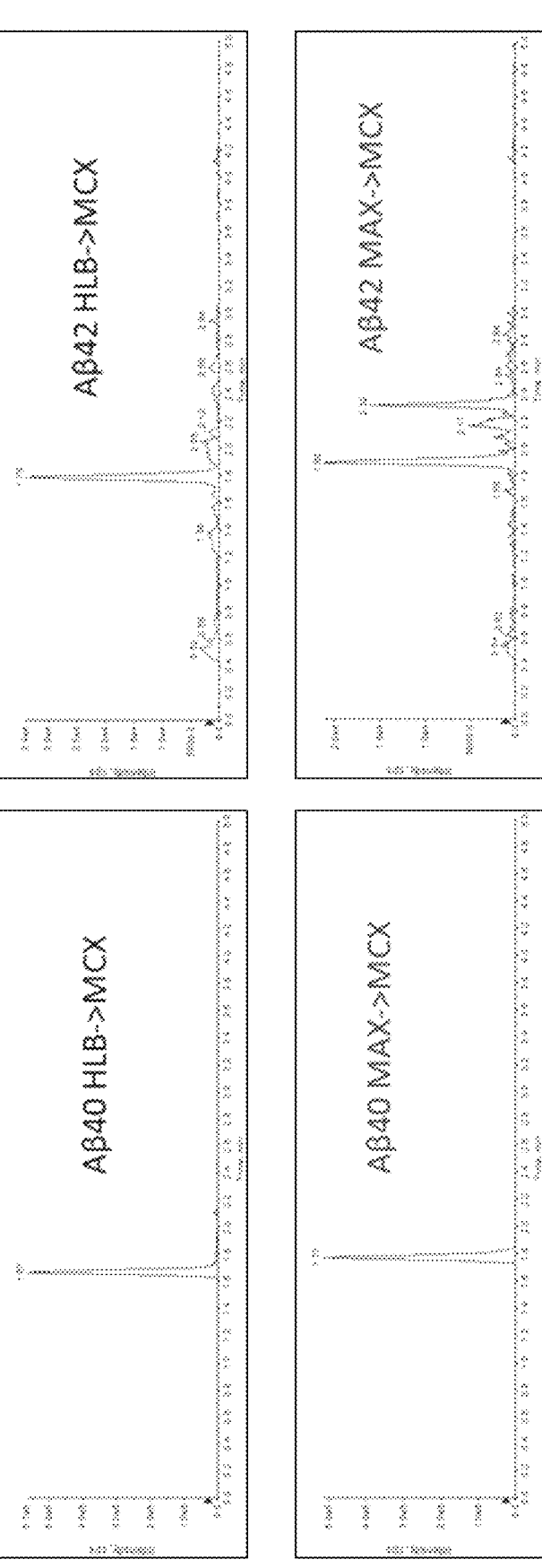
FIG. 7 shows the chromatograms obtained for a plasma sample subjected to a 1$^{st}$ SPE step, a Mixed-Mode Reversed Phase-Anion Exchange SPE (MAX) followed by a second SPE MCX, according to protocol D in comparison with the combination of a first HLB followed by a second MCX. The left trace relates to Aβ40, and the right trace to Aβ42.

FIG. 7 shows the chromatographic traces extracted for Aβ40 (left) and Aβ42 (right) when the plasma sample was contacted with an basic denaturing agent and separated firstly with a Mixed-Mode Reversed Phase-Anion Exchange SPE (MAX) followed by a second Mixed-Mode Reversed Phase-Cation Exchange SPE (MCX), according to Protocol D. For comparison, the traced obtained when a plasma sample denaturalized with a basic agent and separated firstly with a reversed-mode SPE (HLB) following by a second Mixed-Mode Reversed Phase-Cation Exchange SPE (MCX) are also shown in FIG. 7.

These results demonstrate that when the plasma sample is denatured with a basic agent, and then subjected to a first MAX followed by a MCX, the peaks obtained for Aβ40 and Aβ42 are almost as good as for the combination of HLB followed by MCX when the sample is denatured with an acidic agent.

What is claimed is:

1. A method for preparing a plasma sample comprising amyloid beta peptides for analysis by mass spectrometry, wherein the plasma sample comprises intact amyloid beta peptides Aβ40 and Aβ42, comprising:

a) contacting said plasma sample with a denaturing agent to obtain a denatured solution;

b) performing a first solid phase extraction on the denatured solution to recover a first eluate, c) performing a second solid phase extraction step on said first eluate to recover a second eluate, and d) drying said second eluate and processing the dried second eluate for analysis by mass spectrometry to obtain the plasma sample, wherein the first solid phase extraction step is a reversed-phase solid phase extraction and the second solid phase extraction step is a cation exchange solid phase extraction, wherein the first solid phase extraction step is an anion exchange solid phase extraction and the second solid phase extraction step is a cation exchange solid phase extraction, or wherein the first solid phase extraction step is a cation exchange solid phase extraction and the second solid phase extraction step is an anion exchange solid phase extraction, and wherein the denaturing agent is an acidic denaturing agent if the first solid phase extraction step is a reversed-phase solid phase extraction or a cation exchange solid phase extraction, or wherein the denaturing agent is a basic denaturing agent if the first solid phase extraction step is an anion exchange solid phase extraction.

2. The method according to claim 1, wherein the cation or anion exchange solid phase extraction is a strong, weak or Mixed Mode Reversed Phase Ion Exchange.

3. The method according to claim 1, wherein (a) comprises contacting the plasma sample with an acidic denaturing agent such that the denatured solution has a pH of less than or equal to about 4.5.

4. The method according to claim 3, wherein the acidic denaturing agent is a solution of formic acid in water at a concentration between 40% and 70% (v/v).

5. The method according to claim 1, wherein the second solid phase extraction is an anion exchange solid phase extraction and wherein the first and second solid phase extractions each comprise a first wash with a solution comprising an acid and a second wash with a solution comprising a water miscible polar organic solvent.

6. The method according to claim 5, wherein the solution comprising an acid used in the first solid phase extraction is different than the solution used in the second solid phase extraction.

7. The method according to claim 1, wherein the first solid phase extraction is a cation exchange solid phase extraction, and wherein the first solid phase extraction comprises a first wash with a solution comprising an acid and the second solid phase extraction comprises a first wash step with a solution comprising a base, and each of the first and second solid phase extractions further comprises a second wash with a water miscible polar organic solvent.

8. The method according to claim 1, wherein (a) comprises contacting the plasma sample with a basic denaturing agent such that the denatured solution has a pH of more than or equal to about 11.

9. The method according to claim 8, wherein the basic denaturing agent is a solution of ammonium hydroxide in water at a concentration between 5 and 50% (v/v).

10. The method according to claim 1, wherein the first solid phase extraction is an anion exchange solid phase extraction, and wherein the first solid phase extraction comprises a first wash step with a solution comprising a base and the second solid phase extraction comprises a first wash with a solution comprising an acid, and each of the first and second solid phase further comprises a second wash with a solution comprising a water miscible polar organic solvent.

11. The method according to claim 1, wherein the solution for processing the dried eluate is an aqueous solution comprising a surfactant and a reducing agent.

12. The method according to claim 11, wherein the solution for processing the dried eluate is an aqueous solution comprising Triton X-100 at a concentration between 0.01% and 0.8% (v/v) and tris-carboxyethylphosphine at a concentration between 0.1% and 0.2% (w/v).

13. The method according to claim 1, wherein the solution for processing the dried eluate is an aqueous solution comprising a surfactant, a reducing agent, a water miscible polar organic solvent and an acid.

14. The method according to claim 13, wherein the solution for processing the dried eluate is an aqueous solution comprising Triton X-100 at a concentration between 0.01% and 0.8% (v/v), tris-carboxyethylphosphine at a concentration between 0.1% and 0.2% (w/v), acetonitrile at a concentration between 3% and 7% (v/v), dimethylformamide at a concentration between 0.1% and 3% (v/v) and trifluoroacetic acid (TFA) at a concentration between 0.1% and 3% (v/v).

15. The method according to claim 1, wherein the method does not comprise immunoprecipitation or digestion of the plasma sample prior the mass spectrometry analysis.

* * * * *